(12) United States Patent
Hlavinka et al.

(10) Patent No.: US 7,549,956 B2
(45) Date of Patent: Jun. 23, 2009

(54) CENTRIFUGAL SEPARATION APPARATUS AND METHOD FOR SEPARATING FLUID COMPONENTS

(75) Inventors: Dennis Hlavinka, Arvada, CO (US); Thomas J. Felt, Boulder, CO (US)

(73) Assignee: Caridianbct, Inc., Lakewood, CO (US)

( * ) Notice: Subject to any disclaimer, the term of this patent is extended or adjusted under 35 U.S.C. 154(b) by 513 days.

(21) Appl. No.: 11/348,524

(22) Filed: Feb. 7, 2006

(65) Prior Publication Data

US 2006/0191857 A1 Aug. 31, 2006

Related U.S. Application Data

(60) Division of application No. 09/985,050, filed on Nov. 1, 2001, now Pat. No. 7,029,430, which is a continuation of application No. 09/270,105, filed on Mar. 16, 1999, now Pat. No. 6,334,842.

(51) Int. Cl.
*B04B 11/00* (2006.01)
(52) U.S. Cl. ............................................ 494/37; 494/45
(58) Field of Classification Search .................... 494/3, 494/37, 45
See application file for complete search history.

(56) References Cited

U.S. PATENT DOCUMENTS

| | | | |
|---|---|---|---|
| 1,684,870 A | 9/1928 | Lewis | |
| 2,616,619 A | 11/1952 | MacLeod | |
| 2,878,995 A | 3/1959 | Dega | |
| 3,771,715 A | 11/1973 | Baram | |
| 3,823,869 A | 7/1974 | Loison | |
| 3,825,175 A | 7/1974 | Sartory | |
| 4,007,871 A | 2/1977 | Jones et al. | |
| 4,010,894 A | 3/1977 | Kellogg et al. | |

(Continued)

FOREIGN PATENT DOCUMENTS

DE 26 58 926 6/1978

(Continued)

OTHER PUBLICATIONS

Maxim D. Persidsky et al., Separation of Platelet-rich Plasma by Modified Centrifugal Elutriation; Journal of Clinical Apheresis 1:18-24 (1982).

(Continued)

*Primary Examiner*—David L Sorkin
(74) *Attorney, Agent, or Firm*—Finnegan, Henderson, Farabow, Garrett & Dunner, LLP

(57) ABSTRACT

An apparatus and method are provided for separating components of a fluid or particles. A separation vessel having a barrier dam is provided to initially separate an intermediate density components of a fluid, and a fluid chamber is provided to further separate these intermediate density components by forming an elutriative field or saturated fluidized particle bed. The separation vessel includes a shield for limiting flow into the fluid chamber of relatively high density substances, such as red blood cells. The separation vessel also includes a trap dam with a smooth, gradually sloped downstream section for reducing mixing of substances. Structure is also provided for adding additional plasma to platelets and plasma flowing from the fluid chamber. The system reduces clumping of platelets by limiting contact between the platelets and walls of the separation vessel.

8 Claims, 7 Drawing Sheets

U.S. PATENT DOCUMENTS

| | | |
|---|---|---|
| 4,059,967 A | 11/1977 | Rowe et al. |
| 4,091,989 A | 5/1978 | Schlutz |
| 4,094,461 A | 6/1978 | Kellogg et al. |
| 4,146,172 A | 3/1979 | Cullis et al. |
| 4,187,979 A | 2/1980 | Cullis et al. |
| 4,198,972 A | 4/1980 | Herb |
| 4,268,393 A | 5/1981 | Persidsky et al. |
| 4,316,576 A | 2/1982 | Cullis et al. |
| 4,322,298 A | 3/1982 | Persidsky |
| 4,350,283 A | 9/1982 | Leonian |
| 4,356,958 A | 11/1982 | Kolobow et al. |
| 4,386,730 A | 6/1983 | Mulzet |
| 4,387,848 A | 6/1983 | Kellogg et al. |
| 4,413,771 A | 11/1983 | Rohde et al. |
| 4,413,772 A | 11/1983 | Rohde et al. |
| 4,416,654 A | 11/1983 | Schoendorfer et al. |
| 4,419,089 A | 12/1983 | Kolobow et al. |
| 4,421,503 A | 12/1983 | Latham, Jr. et al. |
| 4,425,112 A | 1/1984 | Ito |
| 4,430,072 A | 2/1984 | Kellogg et al. |
| 4,447,221 A | 5/1984 | Mulzet |
| 4,464,167 A | 8/1984 | Schoendorfer et al. |
| 4,610,846 A | 9/1986 | Martin |
| 4,647,279 A | 3/1987 | Mulzet et al. |
| 4,675,117 A | 6/1987 | Neumann et al. |
| 4,680,025 A | 7/1987 | Kruger et al. |
| 4,701,267 A | 10/1987 | Watanabe et al. |
| 4,708,710 A | 11/1987 | Dunn, Jr. |
| 4,708,712 A | 11/1987 | Mulzet |
| 4,798,579 A | 1/1989 | Penhasi |
| 4,808,151 A | 2/1989 | Dunn, Jr. et al. |
| 4,834,890 A | 5/1989 | Brown et al. |
| 4,846,974 A | 7/1989 | Kelley et al. |
| 4,851,126 A | 7/1989 | Schoendorfer |
| 4,885,137 A | 12/1989 | Lork |
| 4,911,833 A | 3/1990 | Schoendorfer et al. |
| 4,915,847 A | 4/1990 | Dillon et al. |
| 4,933,291 A | 6/1990 | Daiss et al. |
| 4,934,995 A | 6/1990 | Cullis |
| 4,936,820 A | 6/1990 | Dennehey et al. |
| 4,936,998 A | 6/1990 | Nishimura et al. |
| 4,939,081 A | 7/1990 | Figdor et al. |
| 4,939,087 A | 7/1990 | Van Wie et al. |
| 5,006,103 A | 4/1991 | Bacehowski et al. |
| 5,076,911 A | 12/1991 | Brown et al. |
| 5,078,671 A | 1/1992 | Dennehey et al. |
| 5,089,146 A | 2/1992 | Carmen et al. |
| 5,100,564 A | 3/1992 | Pall et al. |
| 5,160,310 A | 11/1992 | Yhland |
| 5,203,999 A | 4/1993 | Hugues |
| 5,213,970 A | 5/1993 | Lopez-Berestein et al. |
| 5,217,427 A | 6/1993 | Cullis |
| 5,224,921 A | 7/1993 | Dennehey et al. |
| 5,229,012 A | 7/1993 | Pall et al. |
| 5,260,598 A | 11/1993 | Brass et al. |
| 5,282,982 A | 2/1994 | Wells |
| 5,298,171 A | 3/1994 | Biesel |
| 5,316,666 A | 5/1994 | Brown et al. |
| 5,316,667 A | 5/1994 | Brown et al. |
| 5,360,542 A | 11/1994 | Williamson, IV et al. |
| 5,362,291 A | 11/1994 | Williamson, IV et al. |
| 5,370,802 A | 12/1994 | Brown |
| 5,397,479 A | 3/1995 | Kass et al. |
| 5,409,813 A | 4/1995 | Schwartz |
| 5,437,624 A | 8/1995 | Langley |
| 5,494,592 A | 2/1996 | Latham, Jr. et al. |
| 5,501,795 A | 3/1996 | Pall et al. |
| 5,529,691 A | 6/1996 | Brown |
| 5,547,591 A | 8/1996 | Hagihara et al. |
| 5,549,834 A | 8/1996 | Brown |
| 5,571,068 A | 11/1996 | Bacehowski et al. |
| 5,580,465 A | 12/1996 | Pall et al. |
| 5,587,070 A | 12/1996 | Pall et al. |
| 5,607,830 A | 3/1997 | Biesel et al. |
| 5,628,915 A | 5/1997 | Brown et al. |
| 5,641,414 A | 6/1997 | Brown |
| 5,656,163 A | 8/1997 | Brown |
| 5,674,173 A | 10/1997 | Hlavinka et al. |
| 5,690,835 A | 11/1997 | Brown |
| 5,702,357 A | 12/1997 | Bainbridge et al. |
| 5,704,888 A | 1/1998 | Hlavinka et al. |
| 5,704,889 A | 1/1998 | Hlavinka et al. |
| 5,720,716 A | 2/1998 | Blakeslee et al. |
| 5,722,926 A | 3/1998 | Hlavinka et al. |
| 5,792,038 A | 8/1998 | Hlavinka et al. |
| 5,792,372 A | 8/1998 | Brown et al. |
| 5,858,251 A | 1/1999 | Borchardt et al. |
| 5,904,645 A | 5/1999 | Hlavinka et al. |
| 5,906,570 A | 5/1999 | Langley et al. |
| 5,913,768 A | 6/1999 | Langley et al. |
| 5,939,319 A | 8/1999 | Hlavinka et al. |
| 5,951,877 A | 9/1999 | Langley et al. |
| 5,954,626 A | 9/1999 | Hlavinka |
| 6,053,856 A | 4/2000 | Hlavinka |
| 6,071,422 A | 6/2000 | Hlavinka et al. |
| 6,334,842 B1 | 1/2002 | Hlavinka et al. |
| 6,354,986 B1 | 3/2002 | Hlavinka et al. |

FOREIGN PATENT DOCUMENTS

| | | |
|---|---|---|
| DE | 28 21 055 | 4/1979 |
| DE | 37 00 122 | 7/1988 |
| EP | 0 057 907 | 8/1982 |
| EP | 0 363 120 | 4/1990 |
| EP | 0 406 485 | 1/1991 |
| EP | 0 408 462 | 1/1991 |
| EP | 0 419 346 | 3/1991 |
| WO | WO 94/02157 | 2/1994 |
| WO | WO 94/27698 | 12/1994 |
| WO | WO 96/32198 | 10/1996 |
| WO | WO 96/33023 | 10/1996 |
| WO | WO 96/40402 | 12/1996 |
| WO | WO 96/40403 | 12/1996 |
| WO | WO 97/30748 | 8/1997 |
| WO | WO 97/43045 | 11/1997 |
| WO | WO 98/50163 | 11/1998 |

OTHER PUBLICATIONS

John F. Jemionek et al., Special Techniques for the Separation of Hemopoietic Cells, Current Methodology in Experimental Hematology, 1984, pp. 12-16.

J. Freedman et al., White Cell Depletion of Red Cell and Pooled Random-Donor Platelet Concentrates by Filtration and Residual Lymphocyte Subset Analysis, Transfusion, 1991, vol. 31, No. 5, pp. 433-440.

Nancy M. Heddle et al., The Role of the Plasma from Platelet Concentrates in Transfusion Reactions, The New England Journal of Medicine, vol. 331, No. 10, Sep. 8, 1994, pp. 625-628, 670 and 671.

A. Bruil et al., Asymmetric Membrane Filters for the Removal of Leukocytes From Blood, Journal of Biomed. Materials Research, vol. 25, 1459-1480, 1991.

Sunny Dzik, Leukodepletion Blood Filters: Filter Design and Mechanisms of Leukocyte Removal, Transfusion Medicine Reviews, vol. VII, No. 2, Apr. 1993, pp. 65-77.

Bernard J. Van Wie et al., The Effect of Hematocrit and Recycle on Cell Separations, Plasma Ther. Transfus. Technol. 1986; 7:373-388.

P.D. Drumheller et al., The Effects of RPM and Recycle on Separation Efficiency in a Clinical Blood Cell Centrifuge, Journal of Biomechanical Engineering, Nov. 1987, vol. 109, pp. 324-329.

R.J. Oxford et al., Interface Dynamics in a Centrifugal Cell Separator, Transfusion, Nov.-Dec. 1988, vol. 28, Nov. 6, pp. 588-592.

A. Tulp et al., A Separation Chamber to Sort Cells and Cell Organelles by Weak Physical Forces, V.A. Sector-Shaped Chamber and Its Application to the Separation of Peripheral Blood Cells, Journal of Immunological Methods 69 (1984), pp. 281-295.

Carl G. Figdor et al., Theory and Practice of Centrifugal Elutriation (CE) Factors Influencing the Separation of Human Blood Cells, Cell Biophysics 5, 105-118 (1983).

P.E. Lindahl, On Counter Streaming Centrifugation in the Separation of Cells and Cell Fragments (1956), pp. 411-415.

C. Almici et al., Counterflow Centrifugal Elutriation: Present and Future, Bone Marrow Transplantation 1993, 12:105-108.

Richard J. Sanderson, Separation of Different Kinds of Nucleated Cells from Blood by Centrifugal Elutriation, Cell Separation Methods and Selected Applications, vol. 1, pp. 153-168.

P.C. Keng et al., Characterization of the Separation Properties of the Beckman Elutriator System, Cell Biophysics 3 (1981), pp. 41-56.

Claes, F. Hogman, Leucocyte Depletion of Blood Components, 1994, pp. 1, 156-173.

A.S. Buchanan et al., Principle of a Counter-streaming Centrifuge for the Separation of Particles of Different Sizes, Nature, Apr. 24, 1948, pp. 648-649.

"Cost-Effectiveness of Leukocyte Depletion of Blood Components", Presented at the 1993 AABB Meeting Miami Beach, FL.

Benefits of Leukocyte Filtration for Red Cell and Platelet Blood Products, Transfusion Associated CMV (1994), pp. 1-18.

G. Stack et al., Cytokine Generation in Stored Platelet Concentrates, Transfusion, 1994; 34:20-25.

N. M. Heddle et al., A prospective study to identify the risk factors associated with acute reactions to platelet and red cell transfusions; Transfusion, 1993; 33:794-797.

R. Brown et al., Evaluation of a new separation method utilizing plasma recirculation and autoelutriation, Transfusion, 1994; vol. 34, Supp.

Richard J. Sanderson et al., Design Principles for a Counterflow Centrifugation Cell Separation Chamber; Analytical Biochemistry 71, 615-622(1976).

Haemonetics Mobile Collection System Owner's Operating and Maintenance Manual, 1991 pp. 3-2 through 3-7 and pp. 1-6.

Judy H. Angelbeck, Adverse Reactions to Platelet Transfusion, Risks and Probable Causes (1994), pp. 1-14.

The Mobile Collection System gives you easier access to more donors than ever before, Haemonetics (Sep. 1992).

Brief Operating Instructions, Fresenius MT AS 104 blood cell separator, 4/6.90(OP).

Baxter CS-3000 Plus Blood Cell Separator, Technology With a Mind You Can Own, 1990.

Plas, et al., "A New Multi-chamber Counterflow Centrifugation Rotor with High-separation Capacity and Versatile Potentials," Experimental Hematology 16:355-359 (1988) International Society for Experimental Hematology.

Kauffman, et al., "Isolation of Cell Cycle Fractions by Counterflow Centrifugal Elutriation," Analytical Biochemistry 191, 41-46 (1990).

A. Faradji, et al., "Large Scale Isolation of Human Blood Monocytes by Continuous Flow Centrifugation Leukapherisis and Counterflow Centrifugation Elutriation for Adoptive Cellular Immunotherapy in Cancer Patients," Journal of Immunological Methods 174 (1994) 297-309.

Ino K. Gao, et al., "Implementation of a Semiclosed Large Scale Centrifugal Elutriation System," Journal of Clinical Apheresis 3:154-160 (1987).

Griffith, "Separation of T and B Cells from Human Peripheral Blood by Centrifugal Elutriation," Analytical Biochemistry 87, 97-107 (1978).

Carl G. Figdor, et al., "Isolation of Functionally Different Human Monocytes by Counterflow Centrifugation Elutriation," Blood, vol. 60, No. 1, Jul. 1982.

Bernard John Van Wie, Conceptualization and Evaluation of Techniques for Centrifugal Separation of Blood Cells: Optimum Process Conditions, Recycle and Stagewise Processing, Dissertation, 1982, pp. 27-58.

Cobe Spectra™ Apheresis System, Operator's Manual, For Use with Software Program Revisions 3.0 through 3.9, Feb. 1991, pp. 8-1, and 8-3 through 8-34.

E.A. Burgstaler et al., White Blood Cell Contamination of Apheresis Platelets Colletced of the COBE Spectra, COBE Blood Component a Technology, 1992.

T.H. Price et al., Platelet Collection Using the COBE Spectra, COBE Blood Component Technology, 1988.

Nancy Besso et alk, Asahi Sepacell PL-10A Leukocyte Removal Filter: Effect to Post-Filtration Flush With Saline, PALL Technical Report, 1991.

Harvey J. Brandwein et al., Asahi Sepacell PL-10A Leukocyte Removal Filter Description and Review of Claims, PALL Technical Report, 1991.

"Lower is Better!", (flyer) PALL Biomedical Products Company, 1994.

Centrifugual Elutriation, Beckman pp. 1-7, vi; date determined to be more than a year before Mar. 16, 1999.

AS 104 Cell Separator, Fresenius; date determined to be more than a year before Mar. 16, 1999.

CS-3000 Blood Cell Separator, Powerful Technology, Fenwal Laboratories; date determined to be more than a year before Mar. 16, 1999.

Baxter CS-3000 Plus Blood Cell Separator Operator's Manual (7-19-3-136); date determined to be more than a year before Mar. 16, 1999.

LRF6/LRF10, High Efficiency Leukocyte Removal Filter Systems For Platelets, PALL Biomedical Products Corporation; date determined to be more than a year before Mar. 16, 1999.

J. Whitbread et al., Reduction of C3A Fragment Levels Following Leukodepletion Using a PALL PXL8 Filter; date determined to be more than a year before Mar. 16, 1999.

T. A. Takahashi et al., Bradykinin Formation in a Platelet Concentrate Filtered with a Leukocyte-removal Filter Made of Nonwoven Polyester Fibers with Negatively Charged Surface, 1994.

Baxter CS-3000 Plus Blood Cell Separator pp. 1-18; date determined to be more than a year before Mar. 16, 1999.

J.F. Jemionek, Variations in CCE Protocol for Cell Isolation, Elutriation, 1984, pp. 17-41.

English language abstract of SU 1725117 A, Apr. 7, 1992.

English language abstract of SU 1255136, Sep. 7 ,1986.

English language abstract of SU 1236366, Jun. 7, 1986.

English language abstract of SU 1091071, May 7, 1984.

English language abstract of DE 3734170, Apr. 20, 1989.

Multi Chamber Counterflow Centrifugation System, Dijkstra Vereenigde B.V., 13 pgs; date determined to be more than a year before Mar. 16, 1999.

R.J. Oxford et al., Monitoring and Automated Optimization of a Cell Centrifuge, IEEE/Eighth Annual Conference of the Engineering in Medicine and Biology Society, pp. 925-927, 1986.

Robert J. Grabske, Separating Cell Populations by Elutriation, pp. 1-8, 1978.

Biofil, Systems for Filtration of Haemocomponents; date determined to be more than a year before Mar. 16, 1999.

I. Sniecinski, Prevention of Immunologic and Infectious Complications of Transfusion by Leukocyte Depletion, Prevention of Complications of Transfusion Chapter 18; pp. 202-211, Aug. 1993.

H. Brandwein et al., Asahi Sepacell PL10A Leukocyte Removal Filter:Efficiency with Random Donor Platelet Pools, PALL Technical Report; date determined to be more than a year before Mar. 16, 1999.

J. Whitbread et al., Performance Evaluation of the Sepacell PL10A filter and Pall PXL 8 filter: Measurement of Leukocyte Residuals and Consistency, PALL Technical Report; date determined to be more than a year before Mar. 16, 1999.

Designed to Provide the Reliability and Performance to Harvest a High Yield Component Product, The Haemonetics V50 Apheresis System, 1986.

CENTRIFUGAL SEPARATION APPARATUS AND METHOD FOR SEPARATING FLUID COMPONENTS

This is a divisional application of application Ser. No. 09/985,050, filed Nov. 1, 2001 now U.S. Pat. No. 7,029,430, which is a continuation of U.S. patent application No. 09/270,105, filed Mar. 16, 1999 (Now U.S. Pat. No. 6,334,842), all of which are incorporated herein by reference.

BACKGROUND OF THE INVENTION

1. Field of the Invention

The present invention relates to an apparatus and method for separating components of a fluid. The invention has particular advantages in connection with separating blood components.

This application is related to U.S. Pat. No. 5,674,173, issued on Oct. 7, 1997, U.S. patent application Ser. No. 08/676,039, filed on Jul. 5, 1996 (pending), and U.S. patent application Ser. No. 08/853,374, filed on May 8, 1997 (pending). The entire disclosures of U.S. Pat. No. 5,674,173 and U.S. patent applications Ser. Nos. 08/676,039 and 08/853,374 are incorporated herein by reference.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of processes where particles are either separated from one another or from liquid.

In the medical field, it is often necessary to filter blood. Whole blood consists of various liquid components and particle components. Sometimes, the particle components are referred to as "formed elements". The liquid portion of blood is largely made up of plasma, and the particle components include red blood cells (erythrocytes), white blood cells (including leukocytes), and platelets (thrombocytes). While these constituents have similar densities, their average density relationship, in order of decreasing density, is as follows: red blood cells, white blood cells, platelets, and plasma. In addition, the particle constituents are related according to size, in order of decreasing size, as follows: white blood cells, red blood cells, and platelets. Most current purification devices rely on density and size differences or surface chemistry characteristics to separate and/or filter the blood components.

Numerous therapeutic treatments require groups of particles to be removed from whole blood before either liquid or particle components can be infused into a patient. For example, cancer patients often require platelet transfusions after undergoing ablative, chemical, or radiation therapy. In this procedure, donated whole blood is processed to remove platelets and these platelets are then infused into the patient. However, if a patient receives an excessive number of foreign white blood cells as contamination in a platelet transfusion, the patient's body may reject the platelet transfusion, leading to a host of serious health risks.

Typically, donated platelets are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Centrifuges are effective at separating platelets from whole blood, however they typically are unable to separate all of the white blood cells from the platelets. Historically, blood separation and centrifugation devices are typically unable to consistently (99% of the time) produce platelet product that meets the "leukopoor" standard of less than $5 \times 10^6$ white blood cells for at least $3 \times 10^{11}$ platelets collected.

Because typical centrifuge platelet collection processes are unable to consistently and satisfactorily separate white blood cells from platelets, other processes have been added to improve results. In one procedure, after centrifuging, platelets are passed through a porous woven or non-woven media filter, which may have a modified surface, to remove white blood cells. However, use of the porous filter introduces its own set of problems. Conventional porous filters may be inefficient because they may permanently remove or trap approximately 5-20% of the platelets. These conventional filters may also reduce "platelet viability," meaning that once passed through a filter a percentage of the platelets cease to function properly and may be partially or fully activated. In addition, porous filters may cause the release of brandykinin, which may lead to hypotensive episodes in a patient. Porous filters are also expensive and often require additional time consuming manual labor to perform a filtration process.

Although porous filters are effective in removing a substantial number of white blood cells, they have drawbacks. For example, after centrifuging and before porous filtering, a period of time must pass to give activated platelets time to transform to a deactivated state. Otherwise, the activated platelets are likely to clog the filter. Therefore, the use of at least some porous filters is not feasible in on-line processes.

Another separation process is one known as centrifugal elutriation. This process separates cells suspended in a liquid medium without the use of a membrane filter. In one common form of elutriation, a cell batch is introduced into a flow of liquid elutriation buffer. This liquid which carries the cell batch in suspension, is then introduced into a funnel-shaped chamber located in a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal elutriation separates particles having different sedimentation velocities. Stoke's law describes sedimentation velocity (SV) of a spherical particle as follows:

$$SV = \frac{2}{9} \frac{r^2 (\rho_p - \rho_m) g}{\eta}$$

where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in the Stoke's equation and the density of the particle is not, the size of a cell, rather than its density, greatly influences its sedimentation rate. This explains why larger particles generally remain in a chamber during centrifugal elutriation, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

Further, a Coriolis jetting effect takes place when particles flow into an elutriation chamber from a high centrifugal field toward a lower centrifugal field. The fluid and particles turbulently collide with an inner wall of the chamber facing the rotational direction of the centrifuge. This phenomenon mixes particles within the chamber and reduces the effectiveness of the separation process. Further, Coriolis jetting shunts flow along the inner wall from the inlet directly to the outlet. Thus, particles pass around the elutriative field to contaminate the end product.

Particle mixing by particle density inversion is an additional problem encountered in some prior elutriation processes. Fluid flowing within the elutriation chamber has a decreasing velocity as it flows in the centripetal direction from an entrance port toward an increased cross sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

For these and other reasons, there is a need to improve particle separation.

SUMMARY OF THE INVENTION

The present invention is directed to an apparatus and method that substantially obviate one or more of the limitations and disadvantages of the related art. To achieve these and other advantages and in accordance with the purpose of the invention, as embodied and broadly described herein, the invention includes an apparatus for use with a centrifuge having a rotatable rotor including a retainer. The apparatus comprises a separation vessel for placement in the retainer. The separation vessel has an inlet portion, an outlet portion, and a flow path extending between the inlet portion and the outlet portion. The inlet portion has an inlet port for supplying to the separation vessel a fluid to be separated into components. The outlet portion includes a first wall, a second wall spaced from the first wall, at least three outlet ports for removing separated components of the fluid from the separation vessel, and a shield between one of the outlet ports and the second wall for limiting entry into said one outlet port of at least one relatively high density component of the fluid. The shield has a surface facing said one outlet port. When the separation vessel is placed in the retainer, the surface of the shield is located closer than two of the other outlet ports to the axis of rotation to maintain the surface of the shield out of a layer of the relatively high density fluid component formed in the outlet portion.

In one other aspect, the invention includes a centrifugal separation apparatus having a centrifuge rotor, a retainer on the centrifuge rotor, and a separation vessel in the retainer. The separation vessel includes an inlet portion, an outlet portion, and a trap dam. The outlet portion has a barrier for substantially blocking passage of at least one of the separated components of the fluid, and at least one outlet port for removing at least the blocked component of the fluid from the vessel. The trap dam is located between the outlet port and the inlet portion. The trap dam extends away from the axis of rotation of the rotor to trap relatively low density substances and includes a downstream portion having a relatively gradual slope.

In an additional aspect, the separation vessel further includes a gradual sloped segment across from the trap dam. The gradual sloped segment increases thickness of a layer of the relatively high density fluid component formed across from the trap dam.

In another aspect, the invention includes an apparatus having a separation vessel and a fluid chamber. The separation vessel includes an inlet port, a first outlet port for removing at least relatively intermediate density components of fluid, and a second outlet port for removing at least one relatively low density component of the fluid. A first line is coupled to the first outlet port and also is coupled to an inlet of a fluid chamber for separating the components of the fluid flowing through the first line. A second line is coupled to the second outlet port and is also in flow communication with an outlet of the fluid chamber to mix the relatively low density component of the fluid with substances flowing from the outlet of the fluid chamber.

In yet another aspect, the invention includes a method of separating components of a fluid. In the method, a separation vessel rotates about an axis of rotation and fluid to be separated passes into the vessel. The fluid separates into at least a relatively high density component, a relatively intermediate density component, and a relatively low density component. At least the relatively intermediate density component is removed from the separation vessel via an outlet port. Passage of the relatively high density component into the outlet port is limited with a shield having a surface facing the outlet port. The position of an interface between the high density component and the intermediate density component is controlled so that the surface of the shield is between the interface and the outlet port.

In still another aspect, the high density component includes red blood cells, the intermediate density component includes platelets, and the low density component includes plasma.

In an additional aspect, the invention includes a method wherein at least relatively intermediate density components are removed from the separation vessel via a first outlet port; and at least some of a low density component is removed from the separation vessel via a second outlet port. The removed intermediate density components are flowed into a fluid chamber. At least some of a first subcomponent of the intermediate density components is retained in the fluid chamber, and at least some of a second subcomponent of the intermediate density components is permitted to flow from an outlet of the fluid chamber. The low density component removed from the separation vessel is combined with the second subcomponent flowing from the outlet of the fluid chamber.

In a further aspect of the invention, the first subcomponent includes white blood cells, the second subcomponent includes platelets, and the low density component includes plasma.

In an even further aspect of the invention, an apparatus for use with a centrifuge includes a separation vessel having an outlet portion including at least one outlet port and a shield having a surface facing the outlet port. Structure is provided for controlling the position of an interface between at least one relatively high density component of a fluid and at least one other separated component of the fluid so that the surface of the shield is between the interface and the outlet port.

In another aspect, the invention includes a method of reducing clumping of platelets during separation of blood components. The method includes introducing blood components into a rotating separation vessel such that the blood components stratify in the separation vessel to form at least a radial outer layer including red blood cells, an intermediate layer including at least platelets, and a radial inner layer including low density substances. To substantially limit contact between the platelets and at least one of the radial inner and outer walls of the separation vessel, the radial outer layer of red blood cells is maintained between the intermediate layer and the radial outer wall of the separation vessel and/or the radial inner layer of low density substances is maintained between the intermediate layer and the radial inner wall of the separation vessel. This reduces platelet clumping.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate embodiments of the invention and; together with the description, serve to explain the principles of the invention. In the drawings.

DESCRIPTION OF THE PREFERRED EMBODIMENTS

Figure 1:
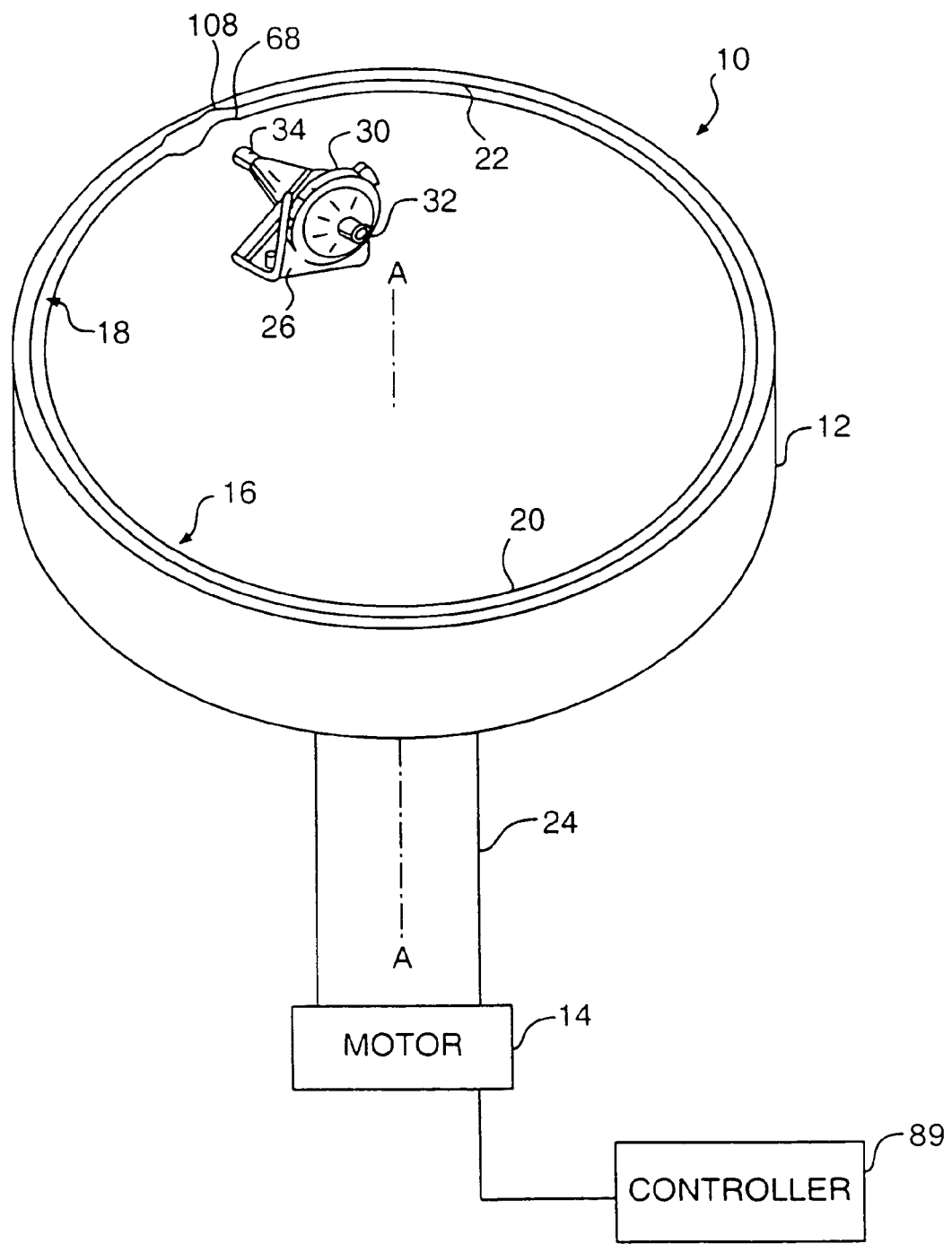
FIG. 1 is a partial perspective view of a centrifuge apparatus including a fluid chamber in accordance with an embodiment of the invention.

Reference will now be made in detail to the present preferred embodiments of the invention illustrated in the accompanying drawings. Wherever possible, the same reference numbers are used in the drawings and the description to refer to the same or like parts, and the same reference numerals with alphabetical suffixes are used to refer to similar parts.

The embodiments of the present invention preferably include a COBE® SPECTRA™ single stage blood component centrifuge manufactured by Cobe Laboratories of Colorado. The COBE® SPECTRA™ centrifuge incorporates a one-omega/two-omega sealless tubing connection as disclosed in U.S. Pat. No. 4,425,112 to Ito, the entire disclosure of which is incorporated herein by reference. The COBE® SPECTRA™ centrifuge also uses a single-stage blood component separation channel substantially as disclosed in U.S. Pat. No. 4,094,461 to Kellogg et al. and U.S. Pat. No. 4,647,279 to Mulzet et al., the entire disclosures of which are also incorporated herein by reference. The embodiments of the invention are described in combination with the COBE® SPECTRA™ centrifuge for purposes of discussion only, and this is not intended to limit the invention in any sense.

As will be apparent to one having skill in the art, the present invention may be advantageously used in a variety of centrifuge devices commonly used to separate blood into its components. In particular, the present invention may be used with any centrifugal apparatus that employs a component collect line such as a platelet collect line or a platelet rich plasma line, whether or not the apparatus employs a single stage channel or a one-omega/two-omega sealless tubing connection.

As embodied herein and illustrated in FIG. 1, the present invention includes a centrifuge apparatus 10 having a centrifuge rotor 12 coupled to a motor 14 so that the centrifuge rotor 12 rotates about its axis of rotation A-A. The rotor 12 has a retainer 16 including a passageway or annular groove 18 having an open upper surface adapted to receive a separation vessel 28, 28a, or 28b shown respectively in FIGS. 2, 4-6, and 7. The groove 18 completely surrounds the rotor's axis of rotation A-A and is bounded by an inner wall 20 and an outer wall 22 spaced apart from one another to define the groove 18 therebetween. Although the groove 18 shown in FIG. 1 completely surrounds the axis; of rotation A-A, the groove could be partially around the axis A-A when the separation vessel is not generally annular. As compared to previous designs of the COBE® SPECTRA™ blood component centrifuge, the outer wall 22 is preferably spaced closer to the axis of rotation A-A to reduce the volume of the separation vessel 28, 28a, 28b and to increase flow velocity in the vessel 28, 28a, 28b.

Preferably, a substantial portion of the groove 18 has a constant radius of curvature about the axis of rotation A-A and is positioned at a maximum possible radial distance on the rotor 12. As described below, this shape ensures that substances separated in the separation vessel 28, 28a, 28b undergo relatively constant centrifugal forces as they pass from an inlet portion to an outlet portion of the separation vessel 28, 28a, 28b.

The motor 14 is coupled to the rotor 12 directly or indirectly through a shaft 24 connected to the rotor 12. Alternately, the shaft 24 may be coupled to the motor 14 through a gearing transmission (not shown).

As shown in FIG. 1, a holder 26 is provided on a top surface of the rotor 12. The holder 26 releasably holds a fluid chamber 30 on the rotor 12 so that an outlet 32 of the fluid chamber 30 is positioned closer to the axis of rotation A-A than an inlet 34 of the fluid chamber 30. The holder 26 preferably orients the fluid chamber 30 on the rotor 12 with a longitudinal axis of the fluid chamber 30 in a plane transverse to the rotor's axis of rotation A-A. In addition, the holder 26 is preferably arranged to hold the fluid chamber 30 on the rotor 12 with the fluid chamber outlet 32 facing the axis of rotation A-A. Although the holder 26 retains the fluid chamber 30 on a top surface of the rotor 12, the fluid chamber 30 may also be secured to the rotor 12 at alternate locations, such as beneath the top surface of the rotor 12.

Figure 2:
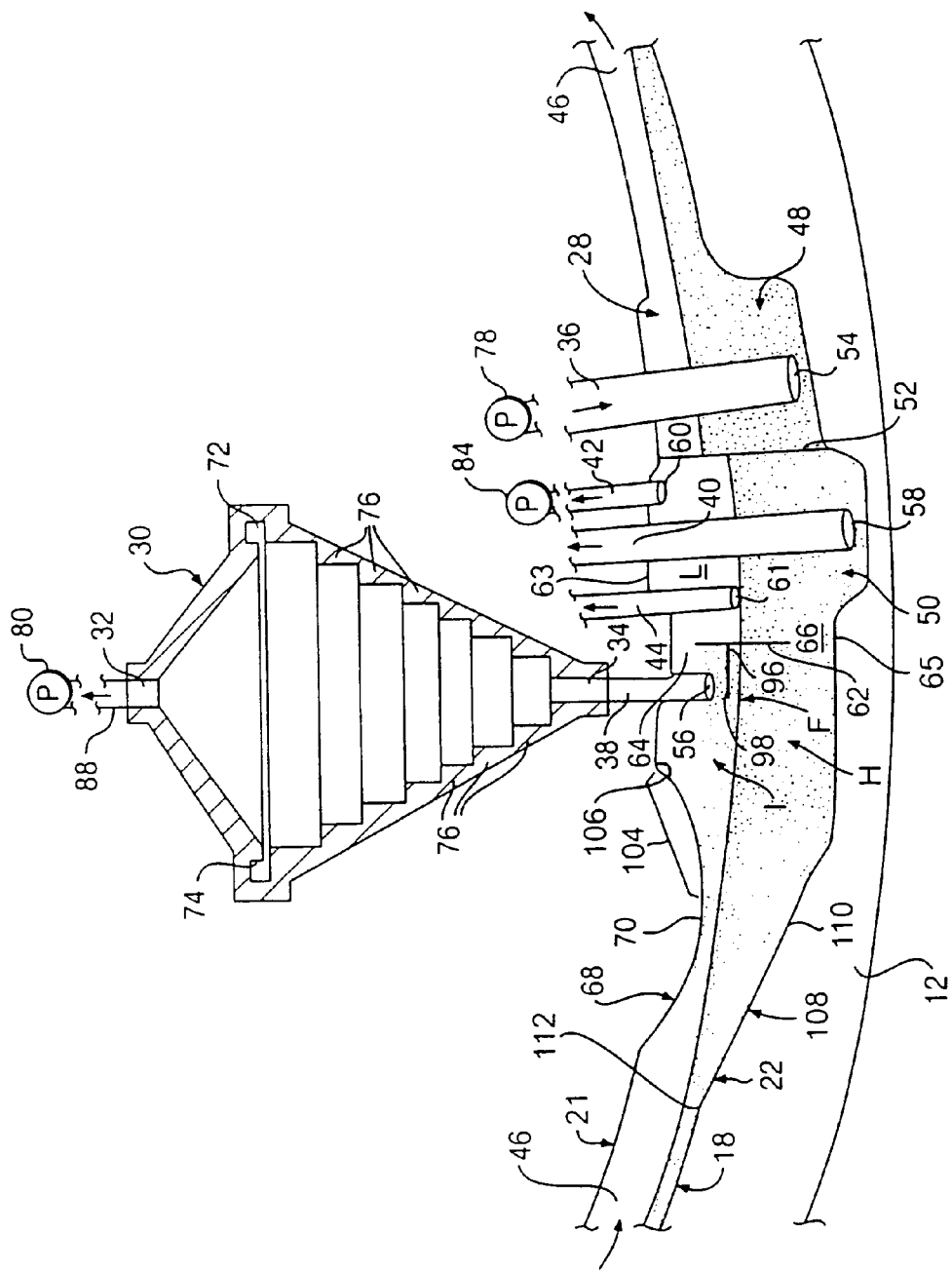
FIG. 2 is a partial cross-sectional, schematic view of a portion of a separation vessel and the fluid chamber mounted on the rotor of FIG. 1 during a separation procedure.

FIG. 2 schematically illustrates a portion of the separation vessel 28 and fluid chamber 30 mounted on the rotor 12. The separation vessel 28 has a generally annular flow path 46 and includes an inlet portion 48 and outlet portion 50. A wall 52 prevents substances from passing directly between the inlet and outlet portions 48 and 50 without first flowing around the generally annular flow path 46 (e.g., counterclockwise as illustrated by arrows in FIG. 2).

In the portion of the separation vessel 28 between the inlet and outlet portions 48 and 50, a radial outer wall 65 of the separation vessel 28 is preferably positioned closer to the axis of rotation A-A than the radial outer wall 65 in the outlet portion 50. During separation of blood components in the separation vessel 28, this arrangement causes formation of a very thin and rapidly advancing red blood cell bed in the separation vessel 28 between the inlet and outlet portions 48 and 50. The red blood cell bed reduces the amount of blood components required to initiate a separation procedure, and also decrease the number of unnecessary red blood cells in the separation vessel 28. As explained below, the radially outer red blood cell bed substantially limits, or more preferably prevents, platelets from contacting the radial outer wall 65 of the separation vessel 28. This is believed to reduce clumping of platelets caused when platelets contact structural components of centrifugal separation devices, which are normally formed of polymer materials.

As shown in FIG. 2, the inlet portion 48 includes an inflow tube 36 for conveying a fluid to be separated, such as whole blood, into the separation vessel 28. The outlet portion 50, on the other hand, includes first, second, and third outlet lines 38, 40, 42 for removing separated substances from the separation vessel 28 and an interface control line 44 for adjusting the level of an interface F between separated substances in the vessel 28. Preferably, the separation vessel 28 forms what is known as a single stage component separation area rather than forming a plurality of such stages. In other words, each of the components separated in the vessel 28 preferably are collected and removed in only one area of the vessel 28, namely the outlet portion 50. In addition, the separation vessel 28 preferably includes a substantially constant radius except in the region of the outlet portion 50 where the outer wall of the outlet portion 50 is preferably positioned farther away from the axis of rotation A-A to allow for outlet ports 56, 58, 60, and 61 of the lines 38, 40, 42, and 44, respectively, to be positioned at different radial distances and to create a collection pool with greater depth for the high density red blood cells.

Although the lines 38, 40, and 42 are referred to as being "collection" lines, the substances removed through these lines can be either collected or reinfused back into a donor. In addition, the invention could be practiced without one or more of the lines 40, 42, and 44.

Although FIG. 2 shows the inlet portion 48 as having a wide radial cross-section, the outer wall of the inlet portion 48 can be spaced closer to the inner wall of the inlet portion 48 and/or be tapered. An inlet port 54 of inflow tube 36 allows for flow of a substance to be separated, such as whole blood, into the inlet portion 48 of separation vessel 28. During a separation procedure, substances entering the inlet portion 48 follow the flow path 46 and stratify according to differences in density in response to rotation of the rotor 12. Preferably, the flow path 46 between the inlet and outlet portions 48 and 50 is curved and has a substantially constant radius. In addition, the flow path 46 is placed at the maximum distance from the axis A-A. This shape ensures that components passing through the flow path 46 encounter a relatively constant gravitational field and a maximum possible gravitational field for the rotor 12.

The separated substances flow into the outlet portion 50 where they are removed via first, second, and third outlet ports 56, 58, and 60 respectively, of first, second, and third collection lines 38, 40, and 42. Separated substances are also removed by an interface controlling outlet port 61 of the interface control line 44.

As shown in FIG. 2, the first, second, and third ports 56, 58, and 60 and interface port 61 are positioned at varying radial locations on the rotor 12 to remove substances having varying densities. The second outlet port 58 is farther from the axis of rotation A-A than the first, third, and interface ports 56, 60 and 61 to remove higher density components H separated in the separation vessel 28, such as red blood cells. The third port 60 is located closer to the axis of rotation A-A than the first, second, and interface ports 56, 58, and 61 to remove the least dense components L separated in the separation vessel 28, such as plasma. Preferably, the first port 56 is about 0.035 inch to about 0.115 inch closer than the interface port 61 to the axis of rotation A-A.

As shown in FIG. 2, the outlet portion 50 includes a barrier 62 for substantially blocking flow of intermediate density components I, such as platelets and some mononuclear cells (white blood cells). Preferably, the barrier 62 is a skimmer dam extending completely across the outlet portion 50 in a direction generally parallel to the axis of rotation A-A. The first outlet port 56 is positioned immediately upstream from barrier 62, downstream from the inlet portion 48, to collect at least the intermediate density components I blocked by the barrier 62 and, optionally, some of the lower density components L.

Radially inner and outer edges of the barrier 62 are spaced from radially inner and outer walls 63, 65 of the separation vessel 28 to form a first passage 64 for lower density components L, such as plasma, at a radially inner position in the outlet portion 50 and a second passage 66 for higher density components H, such as red blood cells, at a radially outer position in the outlet portion 50. The second and third collection ports 58 and 60 are preferably positioned downstream from the barrier 62 to collect the respective high and low density components H and L passing through the second and first passages 66 and 64.

The interface control outlet port 61 is also preferably positioned downstream from the barrier 62. During a separation procedure, the interface port 61 removes the higher density components H and/or the lower density components L in the outlet portion 50 to thereby control the radial position of the interface F between the intermediate density components I and higher density components H in the outlet portion 50 so that the interface F and the interface port 61 are at about the same radial distance from the rotational axis A-A. Although the interface port 61 is the preferred structure for controlling the radial position of the interface F, alternative structure could be provided for performing this function. For example, the position of the interface F could be controlled without using an interface port by providing an optical monitor (not shown) for monitoring the position of the interface and controlling flow of liquid and/or particles through one or more of the ports 54, 56, 58, and 60 in response to the monitored position.

Preferably, the second collection line 40 is flow connected to the interface control line 44 so that substances removed via the second collection port 58 and the interface control port 61 are combined and removed together through a common line. Although the second and third outlet ports 58 and 60 and the interface outlet port 61 are shown downstream from the barrier 62, one or more of these ports may be upstream from the barrier 62. In addition, the order of the outlet ports 56, 58, 60, and the control port 61 along the length of the outlet portion 50 could be changed. Further details concerning the structure and operation of the separation vessel 28 are described in U.S.

Pat. No. 4,094,461 to Kellogg et al. and U.S. Pat. No. 4,647,279 to Mulzet et al., which have been incorporated herein by reference.

A shield 96 is positioned between the first outlet port 56 and the outer wall 65 to limit entry into the first outlet port 56 of the higher density components H. The shield 96 is preferably a shelf extending from an upstream side of the dam 62. In the preferred embodiment, the shield 96 is at least as wide (in a direction parallel to the axis A-A) as the first outlet port 56 and extends upstream at least as far as the upstream end of first outlet port 56 so that the shield 96 limits direct flow into the first outlet port 56 of components residing between the shield 96 and the outer wall 65, including the higher density components H. In other words, the shield 96 ensures that a substantial amount of the substances flowing into the first outlet port 56 originate from radial locations, which are not further than the shield 96 from the axis of rotation A-A.

Preferably, the shield 96 has a radially inner surface 98 facing the first outlet port 56. The inner surface 98 is spaced radially outward from the first outlet port 56 by a distance of preferably from about 0.005 inch to about 0.08 inch, and more preferably from about 0.02 inch to about 0.03 inch. The inner surface 98 is positioned farther than the first and third outlet ports 56 and 60 from the axis of rotation A-A. The inner surface 98 is also positioned closer than the second outlet port 58 and the interface outlet port 61 to the axis of rotation A-A. The relative positioning of the inner surface 98 and interface outlet port 61 maintains the inner surface 98 above the interface F, out of the layer of the higher density components H formed in the outlet portion 50, and in the layer of intermediate density components I. Because the top surface 98 is above the interface F, the shield 96 blocks flow of higher density substances H into the first outlet port 56. When the separation vessel 28 is used in a blood component procedure where the layer of higher density substances H primarily includes red blood cells, preferably the shield 96 significantly reduces the number of red blood cells which flow into the first outlet port 56.

Figure 3:
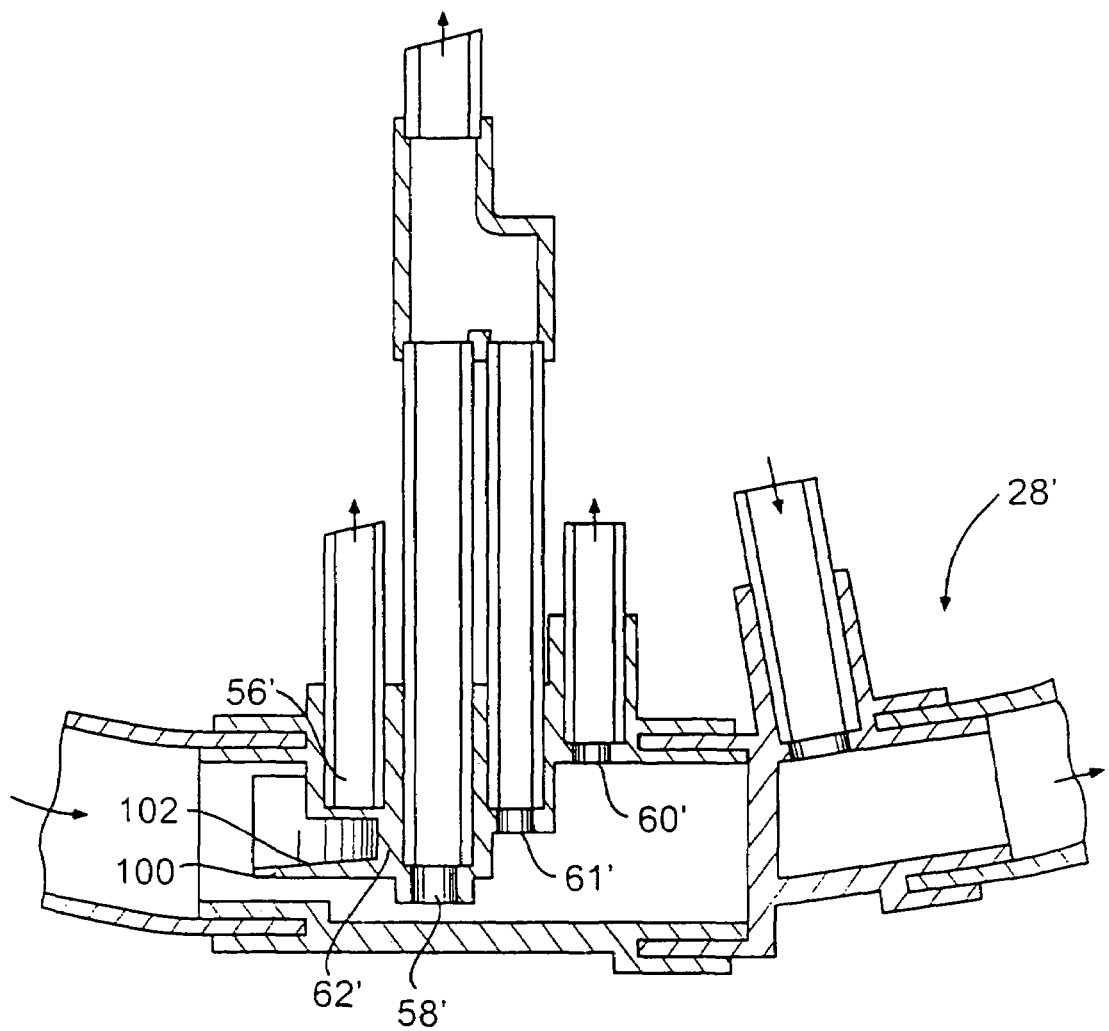
FIG. 3 is a cross-sectional view of inlet and outlet portions of a conventional separation vessel.

FIG. 3 shows a view of a portion of a conventional separation vessel 28' disclosed in above-mentioned U.S. Pat. No. 4,647,279 to Mulzet et al. As shown in FIG. 3, this separation vessel 28' includes a first outlet 56' for intermediate density substances, a second outlet 58' for high density substances, a third outlet 60' for low density substances, and an interface control outlet 61'. In addition, the separation vessel 28' includes a barrier 62' having a flow directer 100 positioned radially outward from the outlet 56'. However, the flow director 100 does not siginificantly reduce flow of high density substances, such as red blood cells, into the outlet 56' because the flow directer 100 has a radially inner surface 102 which is located radially outward from the interface control port 61' to position the inner surface 102 in a layer of higher density substances. In other words, the radially inner surface 102 is located radially outward from an interface between higher density substances and intermediate density substances formed in the separation vessel 28'.

As shown in FIGS. 1 and 2, the preferred embodiment of the present invention preferably includes a ridge 68 extending from the inner wall 20 of the groove 18 toward the outer wall 22 of the groove 18. When the separation vessel 28 shown in FIG. 2 is loaded in the groove 18, the ridge 68 deforms semi-rigid or flexible material in the outlet portion 50 of the separation vessel 28 to form a trap dam 70 on the radially inner wall 63 of the separation vessel 28, upstream from the first collection port 56. The trap dam 70 extends away from the axis of rotation A-A to trap a portion of lower density substances, such as priming fluid and/or plasma, along a radially inner portion of the separation vessel 28 located upstream the trap dam 70.

When the separation vessel 28 is used to separate whole blood into blood components, the trap dam 70 traps priming fluid (i.e. saline) and/or plasma along the inner wall 63 and these trapped substances help convey platelets to the outlet portion 50 and first collection port 56 by increasing plasma flow velocities next to the layer of red blood cells in the separation vessel 28 to scrub platelets toward the outlet portion 50. As explained below, the trapped priming fluid and/or plasma along the inner wall 63 also substantially limits, or more preferably prevents, platelets from contacting the radial inner wall 63. This is believed to reduce clumping of platelets caused when platelets contact structural components of centrifugal separation devices, which are normally formed of polymer materials.

Preferably, the trap dam 70 has a relatively smooth surface to limit disruption of flow in the separation vessel 28, for example, by reducing Coriolis forces. In the preferred embodiment, a downstream portion 104 of the trap dam 70 has a relatively gradual slope extending in the downstream direction toward the axis of rotation A-A. During a blood component separation procedure, the relatively gradual slope of the downstream portion 104 limits the number of platelets (intermediate density components) that become reentrained (mixed) with plasma (lower density components) as plasma flows along the trap dam 70. In addition, the gradual sloped shape of the downstream portion 104 reduces the number of platelets that accumulate in the separation vessel 28 before reaching the first collection port 56.

As shown in FIG. 2, the gradual slope of the downstream portion 104 preferably extends to a downstream end 106 located closer than the first outlet port 56 to the axis of rotation A-A. When the separation vessel 28 is used for blood component separation, the downstream end 106 is preferably located radially inward from the layer of platelets formed in the separation vessel 28. In contrast, when the downstream end 106 is located radially outward from the radially innermost portion of the platelet layer, plasma flowing along the surface of the dam 70 could reentrain (mix) the platelets in plasma downstream from the dam, reducing the efficiency of blood component separation.

In the preferred embodiment shown in FIG. 2, the trap dam 70 and its downstream portion 104 preferably have a generally convex curvature. Preferably, the surface of the trap dam 70 is in the form of a constant radius arc having a center of curvature offset from the axis of rotation A-A. Although the trap dam 70 could have any radius of curvature, a radius of from about 0.25 inch to about 2 inches is preferred, and a radius of about 2 inches is most preferred.

Although the ridge 68 preferably deforms the separation vessel 28 to form the trap dam 70, the trap dam 70 could be formed in other ways. For example, the trap dam 70 could be a permanent structure extending from a radially inner wall of the separation vessel 28. In addition, the trap dam 70 could be positioned closer to the barrier 62 and have a small hole passing therethrough to allow for passage of air in a radial inner area of the outlet portion 50.

As shown in FIGS. 1 and 2, the outer wall 22 of the groove 18 preferably includes a gradual sloped portion 108 facing the ridge 68 in the inner wall 20. When the separation vessel 28 shown in FIG. 2 is loaded in the groove 18, the gradual sloped portion 108 deforms semi-rigid or flexible material in the outlet portion 50 of the separation vessel 28 to form a relatively smooth and gradual sloped segment 110 in a region of the vessel 28 across from the trap dam 70. In an alternative embodiment, this gradual sloped segment 110 is a permanent structure formed in the separation vessel 28.

In the downstream direction, the segment 110 slopes gradually away from the axis of rotation A-A to increase the thickness of a layer of high density fluid components H, such as red blood cells, formed across from the trap dam 70. The gradual slope of the segment 110 maintains relatively smooth flow transitions in the separation vessel 28 and reduces the velocity of high density components H (red blood cells) formed radially outward from the intermediate density components I (platelets).

Preferably, an upstream end 112 of the gradual sloped segment 110 is positioned upstream from the trap dam 70. This position of the upstream end 112 reduces the velocity of high density components H, such as red blood cells, as these components flow past the trap dam 70 and form radially outward from the layer of intermediate density components I blocked by the barrier 62.

As shown in FIG. 2, the first collection line 38 is connected between the first outlet port 56 and the fluid chamber inlet 34 to pass the intermediate density components into the fluid chamber 30. Preferably, the fluid chamber 30 is positioned as close as possible to the first outlet port 56 so that any red blood cells entering the fluid chamber 30 will be placed in a high gravitational field and compacted. As described below, components initially separated in the separation vessel 28 are further separated in the fluid chamber 30. For example, white blood cells could be separated from plasma and platelets in the fluid chamber 30. This further separation preferably takes place by forming an elutriative field in the fluid chamber 30 or by forming a saturated fluidized bed of particles, such as platelets, in the fluid chamber 30.

The fluid chamber 30 is preferably constructed similar or identical to one of the fluid chambers disclosed in above-mentioned U.S. patent application Ser. No. 08/676,039 and U.S. Pat. No. 5,674,173. As shown in FIG. 2, the inlet 34 and outlet 32 of the fluid chamber 30 are arranged along a longitudinal axis of the fluid chamber 30. A wall of the fluid chamber 30 extends between the inlet 34 and outlet 32 thereby defining the inlet 34, the outlet 32, and an interior of the fluid chamber 30.

The fluid chamber 30 preferably includes two frustoconical shaped sections joined together at a maximum cross-sectional area of the fluid chamber 30. The interior of the fluid chamber 30 preferably tapers (decreases in cross-section) from the maximum cross-sectional area in opposite directions toward the inlet 34 and the outlet 32. Although the fluid chamber 30 is depicted with two sections having frustoconical interior shapes, the interior of each section may be paraboloidal, or of any other shape having a major cross-sectional area greater than the inlet or outlet area.

The volume of the fluid chamber 30 should be at least large enough to accommodate the formation of a saturated fluidized particle bed (described below) for a particular range of flow rates, particle sizes, and rotational speeds of the centrifuge rotor 12. The fluid chamber 30 may be constructed from a unitary piece of plastic or from separate pieces joined together to form separate sections of the fluid chamber 30. The fluid chamber 30 may be formed of a transparent or translucent copolyester plastic, such as PETG, to allow viewing of the contents within the chamber interior with the aid of an optional strobe (not shown) during a separation procedure.

As shown in FIG. 2, a groove 72 is formed on an inner surface of the fluid chamber 30 at a position of the maximum cross-sectional area. The groove 72 is defined by top and bottom wall surfaces oriented substantially perpendicular to the longitudinal axis of the fluid chamber 30 and an inner surface of the fluid chamber 30 facing the longitudinal axis. Preferably, the groove 72 is annular, however, the groove 72 may also partially surround the longitudinal axis of the fluid chamber 30.

The groove 72 helps to disperse Coriolis jetting within the fluid chamber 30, as described below. Sudden increases in liquid flow rate during a particle separation procedure may limit the effectiveness of elutriative particle separation or may limit the ability of the saturated fluidized particle bed to obstruct particle passage. Liquid flowing into the fluid chamber 30 undergoes a Coriolis jetting effect. This jetting flow reduces the filtration effectiveness of the saturated fluidized particle bed because liquid and particles may pass between the saturated fluidized particle bed and an interior wall surface of the fluid chamber 30 rather than into the bed itself. The fluid chamber 30 including groove 72 counteracts these effects by channeling Coriolis jetting flow in a circumferential direction partially around the axis of fluid chamber 30. Therefore, the groove 72 improves the particle obstruction capability of the saturated bed, especially when liquid flow rates increase.

As shown in FIG. 2, a circumferential lip 74 extends from a top portion of the groove 72 toward a bottom portion of the groove 72 to define an entrance into the groove 72. The lip 74 functions to guide fluid in the groove 72.

A plurality of steps 76 are preferably formed on an inner surface of the fluid chamber 30 between the maximum cross-section of the chamber 30 and the inlet 34. Although six steps 76 are illustrated, any number of steps may be provided in the fluid chamber 30.

Each step 76 has a base surface oriented substantially perpendicular to the longitudinal axis of the fluid chamber 30, as well as a side surface positioned orthogonal to the base surface. Although FIG. 2 depicts a corner where the side surface and the base surface intersect, a concave groove may replace this corner. In a preferred embodiment, each step 76 is annular and surrounds the axis of the chamber 30 completely to bound a cylindrical shaped area. Alternative, the steps 76 may partially surround the axis of the chamber 30.

Adding steps 76 to the fluid chamber 30, also improves the particle obstruction characteristics of a saturated fluidized particle bed formed in the fluid chamber 30, in particular during increases in the rate of fluid flow. The steps 76 provide this improvement by providing momentum deflecting and redirecting surfaces to reduce Coriolis jetting in fluid chamber 30. When Coriolis jetting takes place, the liquid and particles of the jet travel along an interior surface of the fluid chamber 30 that faces the direction of centrifuge rotation. Therefore, the jet may transport particles between the fluid chamber interior surface and either a saturated fluidized particle bed or an elutriation field positioned in the fluid chamber 30. Thus, particles traveling in the jet may exit the fluid chamber 30 without being separated.

Steps 76 direct or alter the momentum of the Coriolis jet flow of liquid and particles generally in a circumferential direction about the axis of the fluid chamber 30. Thus, a substantial number of particles originally flowing in the jet must enter the saturated fluidized bed or elutriation field to be separated.

The groove 72 and steps 76 are provided to facilitate fluid flow rate increases, as well as to improve steady state performance of the fluid chamber 30. During blood component separation, the groove 72 and steps 76 greatly reduce the number of white blood cells that would otherwise bypass a saturated fluidized platelet bed formed in the fluid chamber 30.

As schematically shown in FIG. 2, a plurality of pumps 78, 80, 84 are provided for adding and removing substances to and from the separation vessel 28 and fluid chamber 30. An inflow pump 78 is coupled to the inflow line 36 to supply a substance to be separated, such as whole blood, to the inlet portion 48. A first collection pump 80 is coupled to outflow tubing 88 connected to the fluid chamber outlet 32. The first collection pump 80 draws fluid and particles from the fluid chamber outlet 32 and causes fluid and particles to enter the fluid chamber 30 via the fluid chamber inlet 34.

A second collection pump 84 is flow coupled to the second collection line 42 for removing substances through the third outlet port 60. Preferably, the second collection line 40 and interface control line 44 are flow connected together, and substances flow through these lines 40 and 44 as a result of positive fluid pressure in the vessel outlet portion 50.

The pumps 78, 80, 84 are preferably peristaltic pumps or impeller pumps configured to prevent significant damage to blood components. However, any fluid pumping or drawing device may be provided. In an alternative embodiment (not shown), the first collection pump 80 may be fluidly connected to the fluid chamber inlet 34 to directly move substances into and through the fluid chamber 30. The pumps 78, 80, 84 may be mounted at any convenient location.

As shown in FIG. 1, the apparatus 10 further includes a controller 89 connected to the motor 14 to control rotational speed of the rotor 12. In addition, the controller 89 is also preferably connected to the pumps 78, 80, 84 to control the flow rate of substances flowing to and from the separation vessel 28 and the fluid chamber 30. The controller 89 preferably maintains a saturated fluidized bed of first particles within the fluid chamber 30 to cause second particles to be retained in the fluid chamber 30. The controller 89 may include a computer having programmed instructions provided by a ROM or RAM as is commonly known in the art.

The controller 89 may vary the rotational speed of the centrifuge rotor 12 by regulating frequency, current, or voltage of the electricity applied to the motor 14. Alternatively, the rotational speed can be varied by shifting the arrangement of a transmission (not shown), such as by changing gearing to alter a rotational coupling between the motor 14 and rotor 12. The controller 89 may receive input from a rotational speed detector (not shown) to constantly monitor the rotation speed of the rotor 12.

The controller 89 may also regulate one or more of the pumps 78, 80, 84 to vary the flow rates for substances supplied to or removed from the separation vessel 28 and the fluid chamber 30. For example, the controller 89 may vary the electricity provided to the pumps 78, 80, 84. Alternatively the controller 89 may vary the flow rate to and from the vessel 28 and the fluid chamber 30 by regulating valving structures (not shown) positioned in the lines 36, 38, 40, 42, 44 and/or 88. The controller 89 may receive input from a flow detector (not shown) positioned within the first outlet line 38 to monitor the flow rate of substances entering the fluid chamber 30. Although a single controller 89 having multiple operations is schematically depicted in the embodiment shown in FIG. 1, the controlling structure of the invention may include any number of individual controllers, each for performing a single function or a number of functions. The controller 89 may control flow rates in many other ways as is known in the art.

Figure 4:
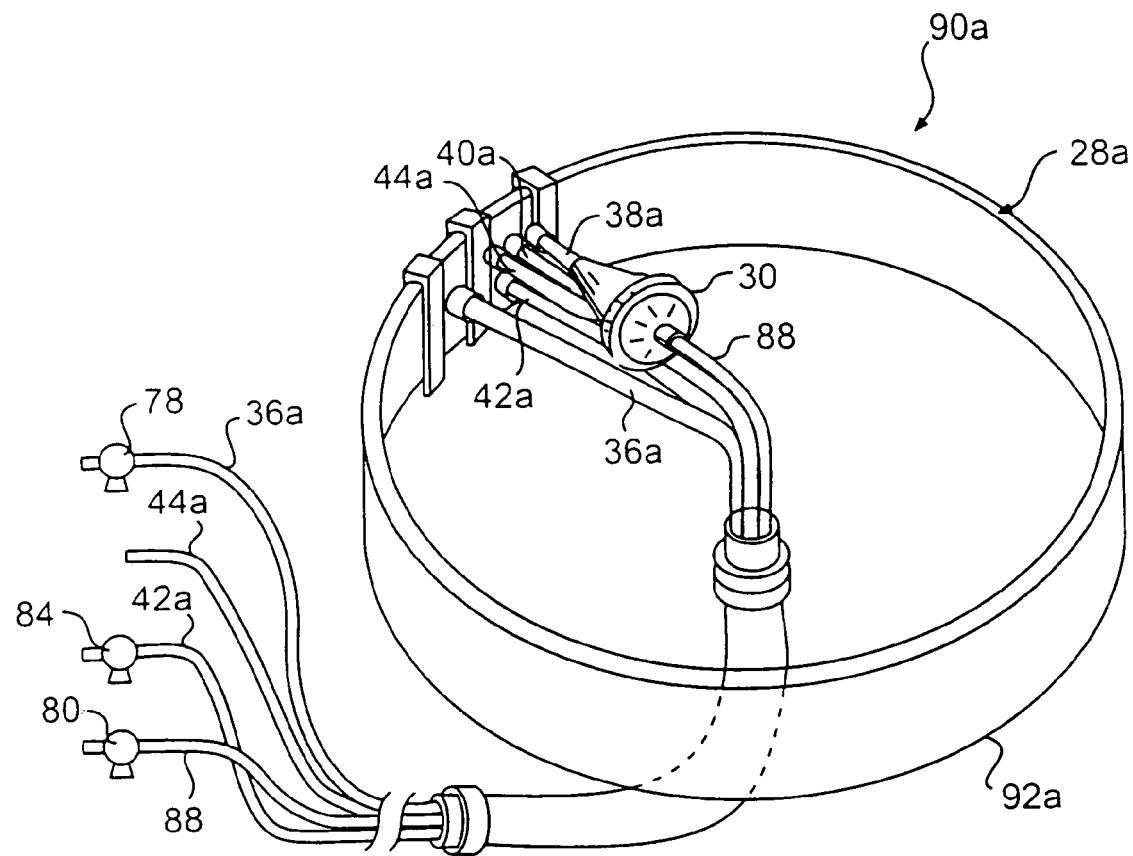
FIG. 4. is a perspective view of a tubing set including the fluid chamber and an alternative embodiment of the separation vessel.
Figure 5:
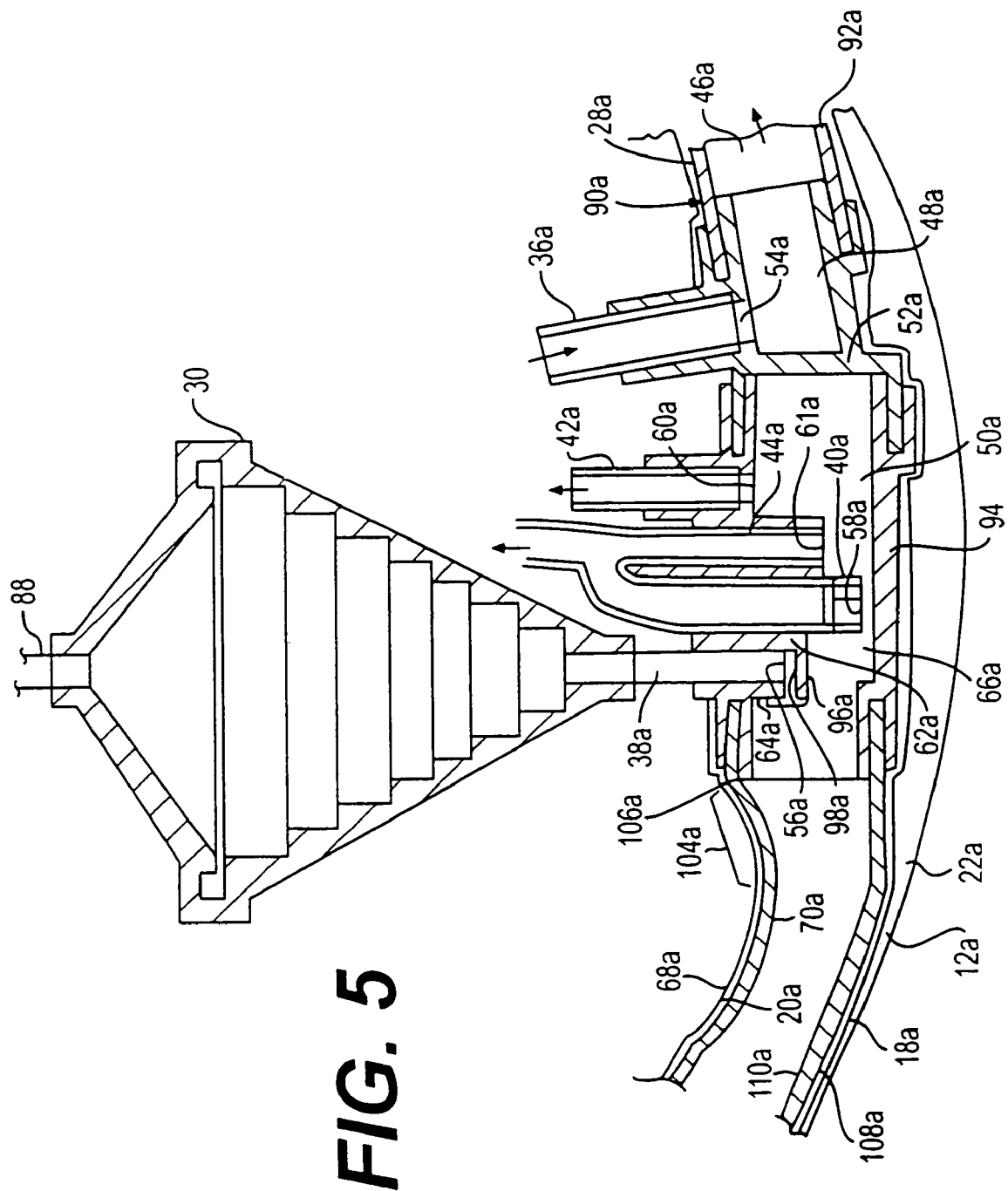
FIG. 5 is a partial cross sectional view of inlet and outlet portions of the separation vessel and fluid chamber of FIG. 4 on a rotor.

FIG. 4 shows an embodiment of a tubing set 90a for use in the apparatus 10, and FIG. 5 illustrates a cross-sectional view of a portion of the tubing set 90a mounted in groove 18a on rotor 12a. The tubing set 90a includes a separation vessel 28a, the fluid chamber 30, an inflow tube 36a for conveying a fluid to be separated, such as whole blood, into the separation vessel 28a, first, second, and third outlet lines 38a, 40a, 42a for removing separated components of the fluid from the separation vessel 28a, and an interface control line 44a for adjusting the level of an interface between separated substances in the vessel 28a. When the separation vessel 28a is mounted on a rotor 12a, the lines 36a, 38a, 42a, and 44a preferably pass through slots (not shown) formed on the rotor 12a.

Preferably, the separation vessel 28a is constructed similar to the centrifugal separator disclosed in above-mentioned U.S. Pat. No. 4,647,279 to Mulzet et al. The separation vessel 28a includes a generally annular channel 92a formed of semi-rigid or flexible material and having a flow path 46a, shown in FIG. 5. Opposite ends of the channel 92a are connected to a relatively rigid connecting structure 94 including an inlet portion 48a and outlet portion 50a for the separation vessel 28a separated by a wall 52a. An inlet port 54a of inflow tubing 36a is in fluid communication with the inlet portion 48a and allows for flow of a substance to be separated, such as blood, into the separation vessel 28a. During a separation procedure, substances entering the vessel 28a via the inlet port 54a flow around the channel 92a (counterclockwise in FIG. 5) via the flow path 46a and stratify according to differences in density in response to rotation of the rotor 12a.

The separated substances flow into the outlet portion 50a where they are removed through first, second and third outlet ports 56a, 58a, and 60a of respective first, second, and third collection lines 38a, 40a, and 42a and an interface control port 61a of the interface control line 44a. As shown in FIG. 5, the second collection line 40a is preferably connected to the interface control line 44a so that substances flowing through the second collection line 40a and interface control line 44a are removed together through a portion of the interface control line 44a.

Figure 6:
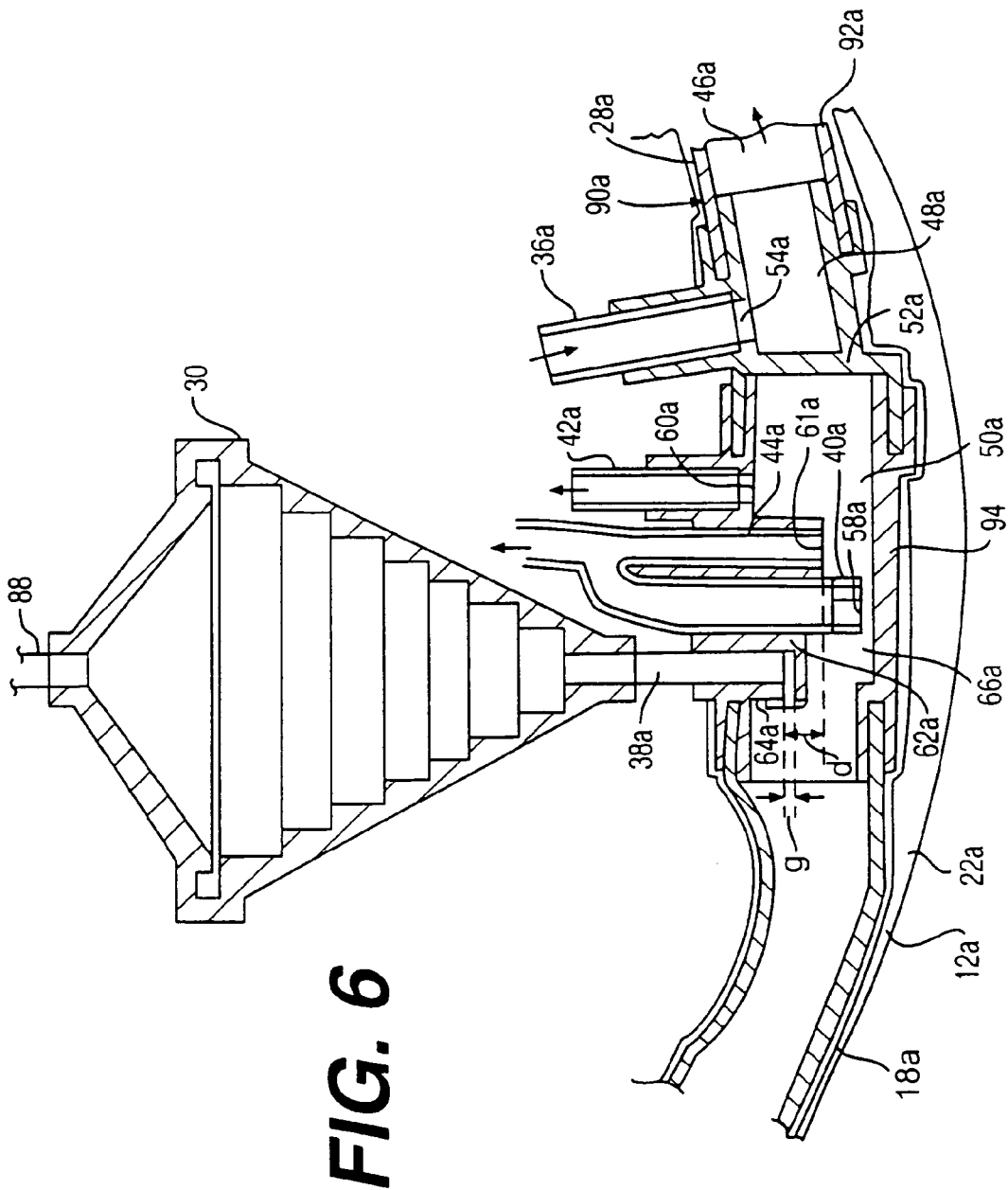
FIG. 6 is a view like that of FIG. 5 showing radial spacing of structural features.

The first, second and third outlet ports 56a, 58a, and 60a and the interface control port 61a have the same relative radial positioning as that of the first, second, and third outlet ports 56, 58, and 60 and the interface control port 61 shown in FIG. 2, respectively. As shown in FIG. 6, the first port 56a and interface port 61a are spaced in the radial direction by a distance "d" of from about 0.035 inch to about 0.115 inch so that the first port 56a is slightly closer to the axis of rotation A-A.

The outlet portion 50a includes a barrier 62a for substantially blocking flow of intermediate density substances, such as platelets and some white blood cells. In the embodiment shown in FIG. 5, the barrier 62a is a skimmer dam extending across the outlet portion 50a in a direction generally parallel to the axis of rotation A-A. The first collection port 56a is positioned immediately upstream from the skimmer dam 62a, and downstream from the inlet portion 48a, to collect the intermediate density substances blocked by the skimmer dam 62a.

A shield 96a extends from the upstream side of the skimmer dam 62a. The shield 96a is preferably configured like the shield 96 shown in FIG. 2 to limit flow of higher density components into the first port 56a. As shown in FIG. 6, the radially inward surface 98a of the shield 96a is spaced radially outward from the first outlet port 56a by a gap "g" of preferably from about 0.005 inch to about 0.08 inch, and more preferably from about 0.02 inch to about 0.03 inch.

Radially inner and outer edges of the skimmer dam 62a are spaced from radially inner and outer walls of the separation vessel 28a to form a first passage 64a for lower density substances, such as plasma, at a radially inner position in the outlet portion 50a and a second passage 66a for higher density substances, such as red blood cells, at a radially outer position in the outlet portion 50a. The second and third collection ports 58a and 60a are preferably positioned downstream from the skimmer dam 62a to collect the respective higher and lower density substances passing through the first and second passages 66a and 64a.

As shown in FIG. 5, a ridge 68a extends from the inner wall 20a of the groove 18a toward the outer wall 22a of the groove 18a. When the separation vessel 28a is loaded in the groove 18a, the ridge 68a deforms the semi-rigid or flexible material of the separation vessel 28a to form a trap dam 70a on the radially inner wall of the separation vessel 28a between the first collection port 56a and the inlet portion of the separation vessel 28a. The trap dam 70a extends away from the axis of rotation A-A to trap a portion of lower density substances, such as priming fluid and/or plasma, along a radially inner portion of the separation vessel 28a. In addition, the trap dam 70a has a gradual sloped downstream portion 104a, and a downstream end 106a located closer than the first outlet port 56a to the axis of rotation A-A. The trap dam 70a preferably has the same or substantially the same structural configuration and function as the trap dam 70 shown in FIG. 2 and could be permanent structure formed in the vessel 28a.

The outer wall 22a preferably includes a gradual sloped portion 108a for forming a corresponding gradual sloped segment 110a in the vessel 28a when the vessel 28a is deformed in the groove 18. The portion 108a and segment 110a have the same or substantially the same structural configuration and function as the portion 108 and segment 110 shown in FIG. 2, respectively.

Figure 7:
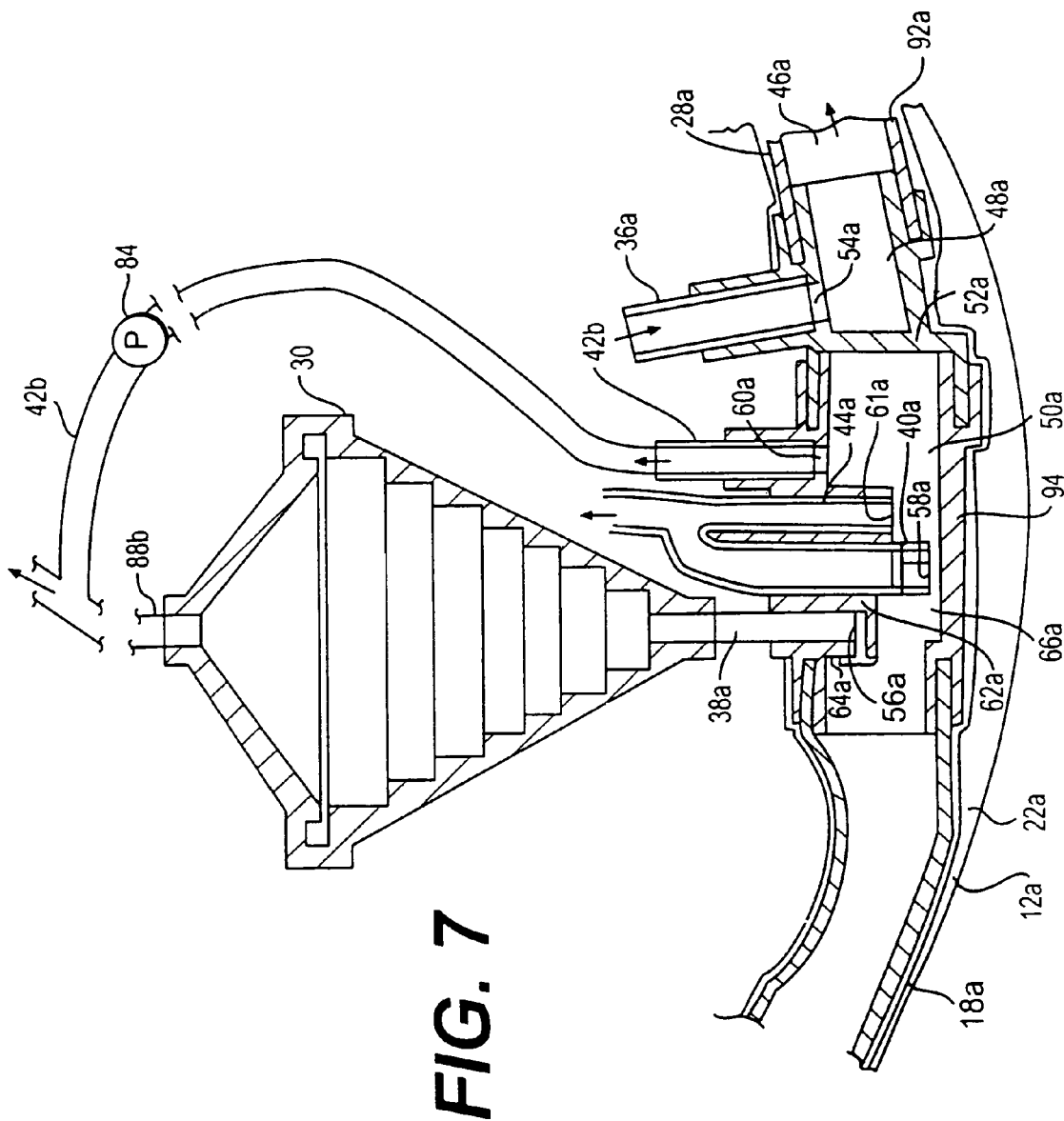
FIG. 7 is a view similar to FIG. 5 of another alternative embodiment.

FIG. 7 shows an embodiment of a separation vessel 28b constructed substantially the same as the separation vessel 28a shown in FIGS. 4-6. In this embodiment, the third collection line 42b is flow coupled to the outflow tubing 88b extending from the fluid chamber outlet 32. This places the third outlet port 60a in flow communication with the fluid chamber outlet 32 to thereby mix substances flowing through the third outlet port 60a with substances flowing through the fluid chamber outlet 32. During a blood component separation procedure, for example, this structural configuration mixes plasma flowing through third port 60a with platelets and plasma flowing from the fluid chamber 30. In certain circumstances, this dilution of the platelet collection may be desired to possibly increase shelf life of the platelet collection.

The fluid chamber outlet 32 and third outlet port 60a could be flow coupled in many different ways. For example, the third collection line 42b could coupled to the outflow tubing 88b upstream from pump 80 shown in FIG. 2 to reduce the concentration of particles being pumped and possibly eliminate pump 84. In the alternative, the outlet of pump 84 could be flow coupled to the outlet of pump 80, for example. Preferably, the flow connection of the third collection line 42b and outflow tubing 88b is not located on the rotatable centrifuge rotor 12a.

Methods of separating components or particles of blood are discussed below with reference to FIGS. 1, 2, and 7. Although the invention is described in connection with blood component separation processes and the structure shown in the drawings, it should be understood that the invention in its broadest sense is not so limited. The invention may be used to separate a number of different particles and/or fluid components, and the structure used to practice the invention could be different from that shown in the drawings. In addition the invention is applicable to both double needle and single needle blood purification or filtration applications. For example, the invention may be practiced with the SINGLE NEEDLE RECIRCULATION SYSTEM FOR HARVESTING BLOOD COMPONENTS of U.S. Pat. No. 5,437,624, the disclosure of which is incorporated herein by reference.

After loading the separation vessel 28 and fluid chamber 30 on the rotor 12, preferably, the separation vessel 28 and chamber 30 are initially primed with a low density fluid medium, such as air, saline solution, plasma, or another fluid substance having a density less than or equal to the density of liquid plasma. Alternatively, the priming fluid is whole blood itself. This priming fluid allows for efficient establishment of a saturated fluidized bed of platelets within the fluid chamber 30. When saline solution is used, the pump 78 shown in FIG. 2 pumps this priming fluid through the inflow line 36 and into the separation vessel 28 via the inlet port 54. The saline solution flows from the inlet portion 48 to the outlet portion 50 (counterclockwise in FIG. 2) and through the fluid chamber 30 when the controller 89 activates the pump 80. Controller 89 also initiates operation of the motor 14 to rotate the centrifuge rotor 12, separation vessel 28, and fluid chamber 30 about the axis of rotation A-A. During rotation, twisting of lines 36, 38, 40, 42, and 88 is prevented by a sealless one-omega/two-omega tubing connection as is known in the art and described in above-mentioned U.S. Pat. No. 4,425,112.

As the separation vessel 28 rotates, a portion of the priming fluid (blood or saline solution) becomes trapped upstream from the trap dam 70 and forms a dome of priming fluid (plasma or saline solution) along an inner wall of the separation vessel 28 upstream from the trap dam 70. After the apparatus 10 is primed, and as the rotor 10 rotates, whole blood or blood components are introduced through the inlet port 54 into the separation vessel 28. When whole blood is used, the whole blood can be added to the separation vessel 28 by transferring the blood directly from a donor through inflow line 36. In the alternative, the blood may be transferred from a container, such as a blood bag, to inflow line 36.

The blood within the separation vessel 28 is subjected to centrifugal force causing components of the blood components to separate. The components of whole blood stratify in order of decreasing density as follows: 1. red blood cells, 2. white blood cells, 3. platelets, and 4. plasma. The controller 89 regulates the rotational speed of the centrifuge rotor 12 to ensure that this particle stratification takes place. A layer of red blood cells (high density component(s) H) forms along the outer wall of the separation vessel 28 and a layer of plasma (lower density component(s) L) forms along the inner wall of the separation vessel 28. Between these two layers, the intermediate density platelets and white blood cells (intermediate density components I) form a buffy coat layer. This separation takes place while the components flow from the inlet portion 48 to the outlet portion 50. Preferably, the radius of the flow path 46 between the inlet and outlet portions 48 and 50 is substantially constant to maintain a steady red blood cell bed in the outlet portion 50 even if flow changes occur.

In the outlet portion 50, platelet poor plasma flows through the first passage 64 and downstream of the barrier 62 where it is removed via the third collection port 60. Red blood cells flow through the second passage 66 and downstream of the barrier 62 where they are removed via the second collection port 58. After the red blood cells, white blood cells, and plasma are thus removed, they are collected and recombined with other blood components or further separated. Alternately, these removed blood components may be reinfused into a donor.

The higher density component(s) H (red blood cells) and lower density component(s) L (plasma) are alternately removed via the interface control port 61 to control the radial position of the interface F between the higher density component(s) H and intermediate density component(s) I (buffy layer). This interface control preferably maintains the radially inner shield surface 98 between the interface F and first outlet port 56.

A substantial portion of the platelets and some of the white blood cells accumulate upstream from the barrier 62. The accumulated platelets are removed via the first outlet port 56 along with some of the white blood cells and plasma. The shield 96 limits passage of higher density substances H (red blood cells) into the first outlet port 56. Preferably, the shield 96 substantially reduces the number of red blood cells entering the first outlet port 56, thereby improving collection purity.

As the platelets, plasma, white blood cells, and possibly a small number or red blood cells pass through the first outlet port 56, these components flow into the fluid chamber 30, filled with the priming fluid, so that a saturated fluidized particle bed may be formed. The portion or dome of priming fluid (i.e. saline) trapped along the inner wall of the separation vessel 28 upstream from the trap dam 70 guides platelets so that they flow toward the barrier 62 and the first outlet port 56. The trapped fluid reduces the effective passageway volume and area in the separation vessel 28 and thereby decreases the amount of blood initially required to prime the system in a separation process. The reduced volume and area also induces higher plasma and platelet velocities next to the stratified layer of red blood cells, in particular, to "scrub" platelets, toward the barrier 62 and first outlet port 56. The rapid conveyance of platelets increases the efficiency of collection.

During a blood component separation procedure, the priming fluid trapped upstream from the trap dam 70 may eventually be replaced by other fluids such as low density, platelet poor plasma flowing in the separation vessel 28. Even when this replacement occurs, a dome or portion of trapped fluid is still maintained upstream from the trap dam 70.

The relatively gradual slope of the downstream portion 104 of the trap dam 70 limits the number of platelets that become reentrained with plasma as plasma flows along the trap dam 70. The downstream portion 104 also reduces the number of platelets accumulated upstream from the barrier 62.

The gradually sloped segment 110 causes formation of a layer of red blood cells across from the trap dam 70. The segment 110 maintains relatively smooth flow transitions in the separation vessel 28 and reduces the velocity of red blood cells in this region.

During a blood component separation procedure, a bed of red blood cells is preferably maintained along the radial outer wall 65 of the separation vessel 28 between the inlet and outlet portions 48 and 50. In addition, the dome or portion of fluid trapped by the trap dam 70 is preferably maintained along the radial inner wall 63 of the separation vessel 28. The bed of red blood cells and trapped fluid substantially limit, or more preferably prevent, platelets from contacting radially outer and inner walls 65 and 63, respectively, because the platelets are sandwiched between the red blood cell bed and trapped fluid. This is believed to reduce platelet clumping caused when platelets come in contract with structural components of centrifugal separation devices, which are formed of conventional polymer materials. Reduction of platelet clumping is significant because it allows for separation of a greater amount of blood components and does not require the use of as much anticoagulant (AC). For example, the present invention is believed to allow for processing of about 20% more blood, as compared to some conventional dual-stage centrifugal separation devices. In addition, the present invention allows for the use of about a 12 to 1 volume ratio of blood components to AC as compared to a 10 to 1 ratio normally used for some conventional dual-stage centrifugal separation devices, for example.

Accumulated platelets, white blood cells, and some plasma and red blood cells, are removed via the first outlet port 56 and flow into the fluid chamber 30 so that the platelets form a saturated fluidized particle bed. The controller 89 maintains the rotation speed of the rotor 12 within a predetermined rotational speed range to facilitate formation of this saturated fluidized bed. In addition, the controller 89 regulates the pump 80 to convey at least the plasma, platelets, and white blood cells at a predetermined flow rate through the first collection line 38 and into the inlet 34 of the fluid chamber 30. These flowing blood components displace the priming fluid from the fluid chamber 30.

When the platelet and white blood cell particles enter the fluid chamber 30, they are subjected to two opposing forces. Plasma flowing through the fluid chamber 30 with the aid of pump 80 establishes a first viscous drag force when plasma flowing through the fluid chamber 30 urges the particles toward the outlet 32. A second centrifugal force created by rotation of the rotor 12 and fluid chamber 30 acts to urge the particles toward the inlet 34.

The controller 89 preferably regulates the rotational speed of the rotor 12 and the flow rate of the pump 80 to collect platelets and white blood cells in the fluid chamber 30. As plasma flows through the fluid chamber 30, the flow velocity of the plasma decreases and reaches a minimum as the plasma flow approaches the maximum cross-sectional area of the fluid chamber 30. Because the rotating centrifuge rotor 12 creates a sufficient gravitational field in the fluid chamber 30, the platelets accumulate near the maximum cross-sectional area of the chamber 30, rather than flowing from the chamber 30 with the plasma. The white blood cells accumulate somewhat radially outward from the maximum cross-sectional area of the chamber 30. However, density inversion tends to mix these particles slightly during this initial establishment of the saturated fluidized particle bed.

The larger white blood cells accumulate closer to inlet 34 than the smaller platelet cells, because of their different sedimentation velocities. Preferably, the rotational speed and flow rate are controlled so that very few platelets and white blood cells flow from the fluid chamber 30 during formation of the saturated fluidized particle bed.

The platelets and white blood cells continue to accumulate in the fluid chamber 30 while plasma flows through the fluid chamber 30. As the concentration of platelets increases, the interstices between the particles become reduced and the viscous drag force from the plasma flow gradually increases. Eventually the platelet bed becomes a saturated fluidized particle bed within the fluid chamber 30. Since the bed is now saturated with platelets, for each new platelet that enters the saturated bed in the fluid chamber 30, a single platelet must exit the bed. Thus, the bed operates at a steady state condition with platelets exiting the bed at a rate equal to the rate additional platelets enter the bed after flowing through inlet 34.

The saturated bed establishes itself automatically, independent of the concentration of particles flowing into the fluid chamber 30. Plasma flowing into the fluid chamber 30 passes through the platelet bed both before and after the platelet saturation point.

The saturated bed of platelets occupies a varying volume in the fluid chamber 30 near the maximum cross-sectional area of the chamber 30, depending on the flow rate and centrifugal field. The number of platelets in the saturated bed depends on a number of factors, such as the flow rate into the fluid chamber 30, the volume of the fluid chamber 30, and rotational speed. If these variables remain constant, the number of platelets in the saturated fluidized bed remains substantially constant. When the flow rate of blood components into the fluid chamber 30 changes, the bed self adjusts to maintain itself by either releasing excess platelets or accepting additional platelets flowing into the fluid chamber 30. For example, when the plasma flow rate into the fluid chamber 30 increases, this additional plasma flow sweeps excess platelets out of the now super-saturated bed, and the bed reestablishes itself in the saturated condition at the increased flow rate. Therefore, the concentration of platelets in the bed is lower due to the release of bed platelets.

After the saturated fluidized bed of platelets forms, flowing plasma carries additional platelets into the fluid chamber 30 and the bed. These additional platelets add to the bed and increase the viscous drag of the plasma flow through the bed. At some point the viscous drag is sufficient to cause platelets near the maximum cross-section area of the fluid chamber 30 to exit the saturated bed and fluid chamber 30. Thus, if the rotational speed and flow rate into the fluid chamber 30 remain constant, the number and concentration of platelets flowing into the saturated fluidized bed of platelets substantially equals the number and concentration of platelets released from the bed.

Although the bed is saturated with platelets, a small number of white blood cells may be interspersed in the platelet bed. These white blood cells, however will tend to "fall" or settle out of the platelet bed toward inlet 34 due to their higher sedimentation velocity. Most white blood cells generally collect within the fluid chamber 30 between the saturated platelet bed and the inlet 34.

Red blood cells in the fluid chamber 30 also settle toward the fluid chamber inlet 34, and some of the red blood cells preferably exit the fluid chamber 30 via the inlet 34 while blood components are entering the chamber 30 via the inlet 34. In other words, bidirection flow into and out of the fluid chamber 30 may take place at the fluid chamber inlet 34.

The controller 89 preferably controls the pump 80 to limit the number of red blood cells accumulating in the fluid chamber 30. For example, the controller 89 can temporarily reverse flow of the pump 80 to cause red blood cells and other dense substances to be flushed from the fluid chamber outlet 34. In addition, the controller 89 may cycle the pump 80 to allow for accumulation of relatively sparse components, such as white blood cells, upstream from the barrier 62.

The saturated fluidized bed of platelet particles formed in the fluid chamber 30 functions as a filter or barrier to white blood cells flowing into the fluid chamber 30. When blood components flow into the fluid chamber 30, plasma freely passes through the bed. However, the saturated fluidized platelet bed creates a substantial barrier to white blood cells entering the fluid chamber 30 and retains these white blood cells within the fluid chamber 30. Thus, the bed effectively filters white blood cells from the blood components continuously entering the fluid chamber 30, while allowing plasma and platelets released from the saturated bed to exit the chamber 30. This replenishment and release of platelets is referred to as the bed's self-selecting quality. Substantially all of these filtered white blood cells accumulate within the fluid chamber 30 between the saturated fluidized platelet bed and the inlet 34.

The particle separation or filtration of the saturated fluidized particle bed obviates a number of limitations associated with prior art elutriation. For example, particles may be separated or filtered in a continuous steady state manner without batch processing. In addition, an additional elutriating fluid medium is not required. Furthermore, after the saturated fluidized particle bed is established, flow rates may be varied over a range without changing the size of the particles leaving the fluid chamber 30. Unlike prior art elutriation, the present invention establishes a saturated particle bed consisting of numerically predominant particles. This bed automatically passes the predominant particles while rejecting larger particles.

The apparatus and method of the invention separate substantially all of the white blood cells from the platelets and plasma flowing through the fluid chamber 30. The barrier to white blood cells is created, at least in part, because white blood cells have a size and sedimentation velocity greater than that of the platelets forming the saturated fluidized particle bed. Therefore, particles of similar densities are separated according to different sizes or sedimentation velocities.

Because the initial separation at barrier 62 and the saturated fluidized bed remove a majority of the red blood cells and some white blood cells, the fluid exiting the fluid chamber 30 consists mainly of plasma and platelets. Unlike some conventional porous filters, where the filtered white blood cells are retained in the filter, the present invention allows a substantial fraction of white blood cells to be recovered and returned to the donor.

When the blood components are initially separated within the separation vessel 28, a substantial number of platelets may become slightly activated. The saturated fluidized platelet bed allows white blood cells to be filtered from plasma and platelets despite this slight activation. Thus, the present invention does not require a waiting period to filter white blood cells after blood components undergo initial separation in a separation vessel 28. This is in contrast to methods using some conventional filters.

After separation, the platelets and plasma exiting the fluid chamber 30 are collected in appropriate containers and stored for later use. The red blood cells and plasma removed from the vessel 28 may be combined for donor reinfusion or storage. Alternatively, these components may be further separated by the apparatus 10.

If dilution of the platelet concentration is desired, the separation vessel 28b shown in FIG. 7 may be used to combine plasma removed via the third outlet port 60a with the platelets and plasma flowing from the fluid chamber outlet 32. This allows for the dilution to take place rapidly without significant intervention by a procedurist.

At the completion of a separation procedure, platelets in the saturated fluidized bed are harvested to recover a substantial number of platelets from the fluid chamber 30. During bed harvest, the controller 89 increases the flow rate and/or decreases the rotational speed of the rotor 12 to release platelets from the bed. This flushes from the fluid chamber 30 most of the platelets that made up the saturated fluidized bed to substantially increase platelet yield. The harvesting continues until substantially all of the platelets are removed, and just before an unacceptable number of white blood cells begin to flow from the fluid chamber 30.

The remainder of contents of the fluid chamber 30, having a high concentration of white blood cells, can be separately collected for later use or recombined with the blood components removed from vessel 28 for return to a donor.

Although the inventive device and method have been described in terms of removing white blood cells and collecting platelets, this description is not to be construed as a limitation on the scope of the invention. The invention may be used to separate any of the particle components of blood from one another. For example, the saturated fluidized bed may be formed from red blood cells to prevent flow of white blood cells through the fluid chamber 22, so long as the red blood cells do not rouleau (clump) excessively. Alternatively, the liquid for carrying the particles may be saline or another substitute for plasma. In addition, the invention may be practiced to remove white blood cells or other components from a bone marrow harvest collection or an umbilical cord cell collection harvested following birth. In another aspect, the invention can be practiced to collect T cells, stem cells, or tumor cells. Further, one could practice the invention by filtering or separating particles from fluids unrelated to either blood or biologically related substances.

It will be apparent to those skilled in the art that various modifications and variations can be made to the structure and methodology of the present invention without departing from the scope or spirit of the invention. For example, the fluid chamber 30 of the invention may be used in a separation process involving elutriation or any other particle separation means without departing from the scope of the invention. Certain aspects of the invention could also be practiced without the fluid chamber. The invention, in its broadest sense, may also be used to separate many different types of particles and/or components from one another. In addition, the abovementioned separation vessels 28, 28a, and 28b may be generally belt shaped and have the inlet portion and outlet portion in separate ends spaced from one another without having the inlet portion connected directly to the outlet portion to form a generally annular shape. Thus, it should be understood that the invention is not limited to the examples discussed in this specification. Rather, the invention is intended to cover modifications and variations provided they come within the scope of the following claims and their equivalents.

What is claimed is:

1. A method of reducing clumping of platelets during separation of blood components, comprising:
   providing a separation vessel including an inlet portion, an outlet portion, and a flow path between the inlet and outlet portions;
   rotating the separation vessel about an axis of rotation;
   introducing blood components into the rotating separation vessel such that the blood components stratify in the separation vessel to form at least a radial outer layer including red blood cells, an intermediate layer including at least platelets, and a radial inner layer including low density substances;
   removing the platelets from the separation vessel via an outlet port in the outlet portion;
   maintaining the radially outer layer of red blood cells between the intermediate layer and a radially outer wall of the separation vessel to substantially limit contact between the platelets and the radially outer wall of the separation vessel and thereby reduce platelet clumping; and
   maintaining the radial inner layer of low density substances between the intermediate layer and a radially inner wall of the separation vessel to substantially limit contact between the platelets and the radially inner wall of the separation vessel and thereby reduce platelet clumping,
   wherein the maintaining of the radially inner layer of low density substances includes trapping the low density substances with a trap dam.

2. The method of claim 1, wherein the low density substances include at least one of saline and plasma.

3. The method of claim 1, wherein the radially outer layer of red blood cells is maintained along the radially outer wall of the separation vessel between the inlet and the outlet portions.

4. The method of claim 1, wherein the layers cause increased platelet velocities and scrubbing of platelets toward the outlet port.

5. A method of reducing clumping of platelets during separation of blood components, comprising:
   providing a separation vessel including an inlet portion, an outlet portion, and a flow path between the inlet and outlet portions;
   rotating the separation vessel about an axis of rotation;
   introducing blood components into the rotating separation vessel such that the blood components stratify in the separation vessel to form at least a radial outer layer including high density substances, an intermediate layer including at least platelets, and a radial inner layer including low density substances;
   removing the platelets from the separation vessel via an outlet port in the outlet portion; and
   maintaining the radially inner layer of low density substances between the intermediate layer and a radially inner wall of the separation vessel to substantially limit contact between the platelets and the radially inner wall of the separation vessel and thereby reduce platelet clumping,
   wherein the maintaining of the radially inner layer of low density substances includes trapping the low density substances with a trap dam.

6. The method of claim 5, wherein the low density substances include at least one of saline and plasma.

7. The method of claim 5, wherein the radially inner layer of low density substances is maintained along the radially inner wall of the separation vessel.

8. The method of claim 5, wherein the layers cause increased platelet velocities and scrubbing of platelets toward the outlet port.

* * * * *

UNITED STATES PATENT AND TRADEMARK OFFICE
CERTIFICATE OF CORRECTION

PATENT NO. : 7,549,956 B2  Page 1 of 1
APPLICATION NO. : 11/348524
DATED : June 23, 2009
INVENTOR(S) : Hlavinka et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 513 days Delete the phrase "by 513 days" and insert -- by 692 days --

Signed and Sealed this

Twentieth Day of April, 2010

David J. Kappos
*Director of the United States Patent and Trademark Office*